(12) United States Patent
Ishikawa et al.

(10) Patent No.: US 7,599,050 B2
(45) Date of Patent: Oct. 6, 2009

(54) SURFACE DEFECT INSPECTING METHOD AND DEVICE

(75) Inventors: Chie Ishikawa, Ibaraki (JP); Makoto Iwata, Kawanishi (JP); Mamoru Sakaue, Mino (JP); Keisuke Kuroki, Takarazuka (JP)

(73) Assignee: Daihatsu Motor Co., Ltd., Osaka (JP)

( * ) Notice: Subject to any disclaimer, the term of this patent is extended or adjusted under 35 U.S.C. 154(b) by 0 days.

(21) Appl. No.: 10/576,486

(22) PCT Filed: Oct. 20, 2004

(86) PCT No.: PCT/JP2004/015466

§ 371 (c)(1),
(2), (4) Date: Dec. 21, 2006

(87) PCT Pub. No.: WO2005/038445

PCT Pub. Date: Apr. 28, 2005

(65) Prior Publication Data

US 2007/0206182 A1    Sep. 6, 2007

(30) Foreign Application Priority Data

Oct. 21, 2003  (JP) ............................. 2003-360584
Mar. 31, 2004  (JP) ............................. 2004-105450
Mar. 31, 2004  (JP) ............................. 2004-105451
Mar. 31, 2004  (JP) ............................. 2004-105452

(51) Int. Cl.
*G01N 21/00*  (2006.01)
(52) U.S. Cl. ................ 356/237.2; 356/237.6; 356/603; 356/606
(58) Field of Classification Search ... 356/237.2–237.6, 356/603–606
See application file for complete search history.

(56) References Cited

U.S. PATENT DOCUMENTS

| 4,918,321 A | | 4/1990 | Klenk et al. |
| 5,691,811 A | * | 11/1997 | Kihira ..................... 356/239.1 |
| 5,963,328 A | * | 10/1999 | Yoshida et al. ........... 356/237.2 |
| 2002/0158198 A1 | * | 10/2002 | Kohama et al. ............. 250/307 |

FOREIGN PATENT DOCUMENTS

| JP | 1038638 A | 2/1989 |
| JP | 2088947 A | 3/1990 |
| JP | 6043119 A | 2/1994 |

(Continued)

*Primary Examiner*—Gregory J Toatley, Jr.
*Assistant Examiner*—Yabo S Alli
(74) *Attorney, Agent, or Firm*—The Webb Law Firm

(57) ABSTRACT

A method of inspecting an inspection target surface comprises: irradiating an irradiation light having a predetermined pattern on the inspection target surface; imaging the surface irradiated with the irradiation light; and inspecting the inspection target surface based on an obtained image of the inspection target surface. The irradiation light irradiated from an irradiation face has a mesh-like pattern including meshes of a same shape. Each mesh has an irradiation area smaller than a non-irradiation area in a plane normal to the optical axis. The inspection target surface is inspected based on lightness/darkness information of an image area in the obtained image corresponding to a non-irradiated area in the inspection target surface. A light point having intermediate brightness and formed in a dark face formed within the mesh is extracted as a defect candidate.

11 Claims, 15 Drawing Sheets

FOREIGN PATENT DOCUMENTS

| | | |
|---|---|---|
| JP | 06-242019 | 9/1994 |
| JP | 8128916 A | 5/1996 |
| JP | 08-145906 | 6/1996 |
| JP | 09-126744 | 5/1997 |
| JP | 10009837 A | 1/1998 |
| JP | 11023243 A | 1/1999 |
| JP | 00-136917 | 5/2000 |
| JP | 00-321037 | 11/2000 |
| JP | 01-059717 | 3/2001 |
| JP | 2001209794 OA | 8/2001 |
| JP | 2002318201 A | 10/2002 |
| JP | 2005127738 A | 5/2005 |
| JP | 2006343185 A | 12/2006 |
| WO | WO 00-136917 | 5/2000 |

* cited by examiner

Fig. 15
(a) original image
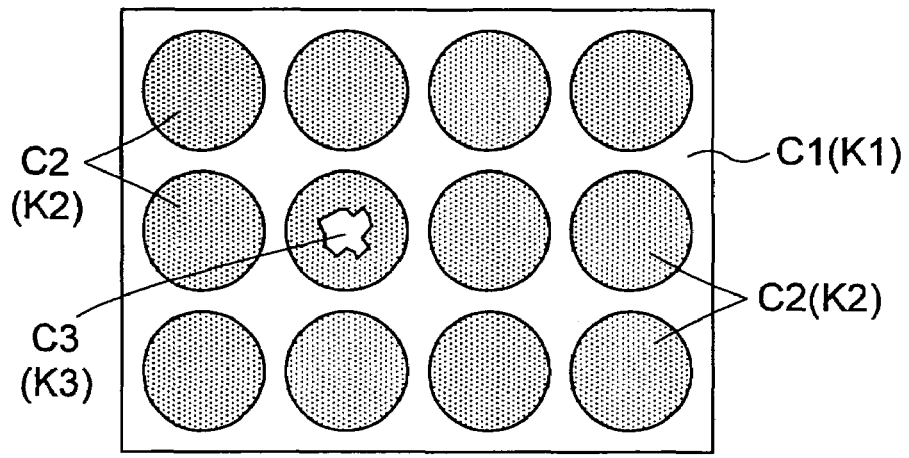
(b) ternarizing operation
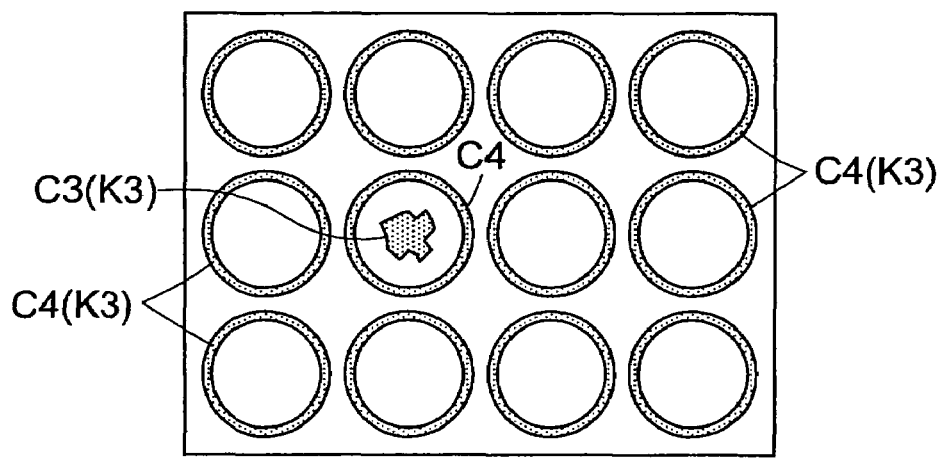
(c) expanding/contracting operation
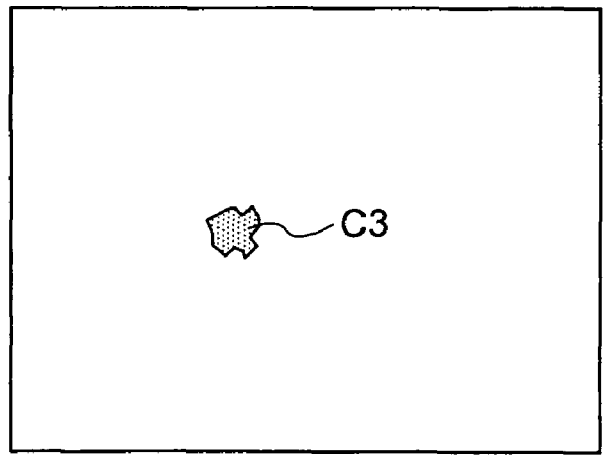

Fig. 16
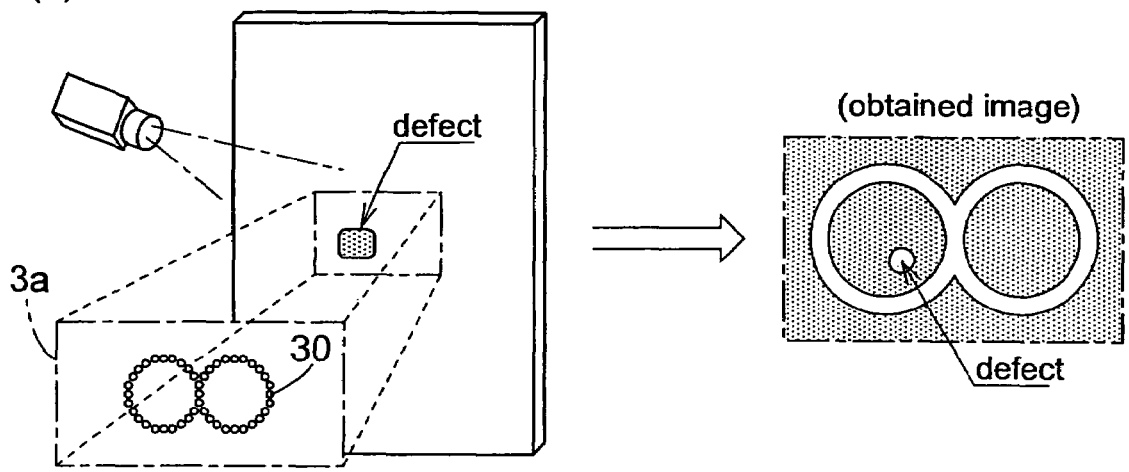
(a)
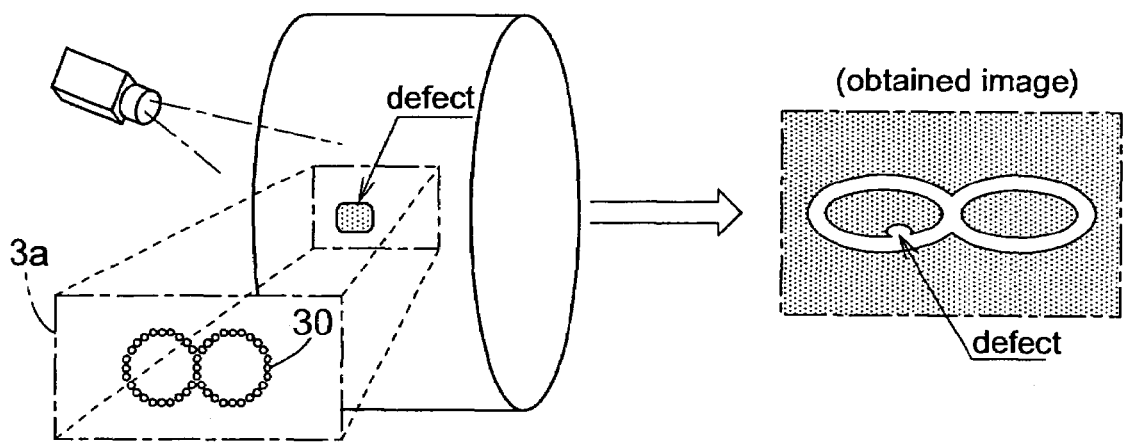
(b)
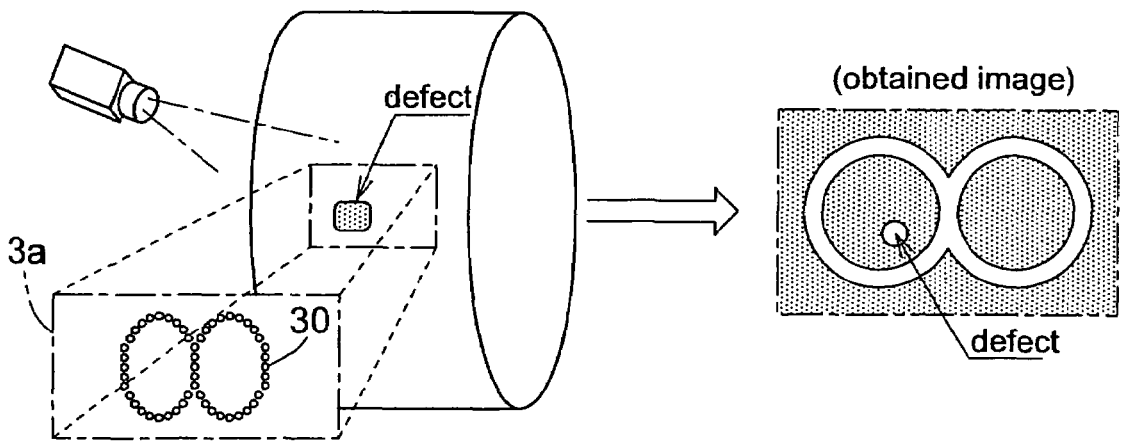
(c)

PRIOR ART

SURFACE DEFECT INSPECTING METHOD AND DEVICE

TECHNICAL FIELD

The present invention relates to a technique of inspecting a surface defect by irradiating an irradiation light having a predetermined layout pattern on an inspection target surface and imaging the surface irradiated with the irradiation light.

BACKGROUND ART

As a typical example of the surface defect inspection of the above-noted type, there can be cited a technique employed for inspection of a painted surface of an automobile body (specifically, its bumper). The inspection target of such surface defect inspection is e.g. unevenness, a scar, etc. present on the painted surface as the inspection target surface.

As an inspection technique using an irradiation light which forms a pattern on the irradiated surface, there is known a technique including the steps of irradiating the painted surface with an irradiation light forming the so-called stripe-like, i.e. horizontal-stripes like lightness/darkness, imaging the irradiated painted surface by an imaging camera and inspecting the surface by using the obtained image.

A specific construction of such inspection system is shown in FIG. 17.

In this defect inspection system shown in FIG. 17, a charging worker 204 takes out a bumper 1, when needed, from a stock station 202 where a plurality of bumpers as inspection targets are stocked, and sets it to a robot 22 which can change its posture, with holding the bumper 1.

The robot 22, while holding the bumper 1, changes the posture of the bumper 1 by rotating it about a rotational axis 22d shown in FIG. 17. The system includes an irradiation apparatus 220 operable to irradiate an irradiation light with a predetermined horizontal-stripe pattern, in association with the above change in the posture. In the illustrated example, this apparatus 220 is disposed so as to surround a moving space within which the posture of the bumper 1 is changed. The irradiation pattern of the irradiation light is a stripe-like lightness/darkness pattern parallel with the rotational axis 22d of the bumper 1.

At predetermined positions of the irradiation apparatus 220, there are provided a plurality of imaging cameras 4. With these cameras 4, the images of the lightness/darkness pattern of the irradiation light reflected off the bumper 1 are obtained. The results of these imaging operations are sent to an analyzing section where evaluation of presence/absence of a defect is carried out.

Upon completion of the above-described retention/posture change by the robot 22, an inspecting worker 201 positioned downstream of the robot 22 removes the bumper 1 from the robot and forwards this to a subsequent process such as a visual inspection.

At the time described above, the inspecting worker 201 has obtained evaluation information from defect evaluating means. Hence, as the worker has already obtained information needing attention in the inspection, the worker can proceed in the process speedily and reliably.

FIG. 18 illustrates the basic principle of the surface defect inspection of the above-described construction.

As shown in this figure, as the painted surface is moved along a predetermined direction (e.g. the direction R), an image portion of a defect such as unevenness on the painted surface is imaged while varying the coordinate of that direction (R coordinate) without changing the coordinate in the direction (e.g. the direction of the two sides of the plane of FIG. 18) normal to the moving direction R. With this, the defect can be detected.

That is, the defect is discriminated by utilizing the fact that the defect area will appear dark in a light stripe portion or will appear light in a dark stripe portion in the obtained image. Hence, the defect can be recognized as an intermediate gradation image in the light portion or the dark portion in the stripes. A technique utilizing a similar inspection principle is disclosed in Patent Document 1.

Further, for the purpose of detecting a defect called "orange peel" which is periodical unevenness in the surface, there is known a technique of detecting non-uniformity in the paint thickness through fluctuation of a lightness/darkness stripes as an irradiation light at a border line in the obtained image (see Patent Document 2).

With this inspection method, there is no need for moving the inspection target surface. However, this method is directed mainly for such a painted surface having a disturbance which causes a displacement of the border line image of the stripes over a relatively large area in the painted surface.

Patent Document 1: Japanese Patent Application "Kokai" No. 8-145906 (FIGS. 5, 9 and 15).

Patent Document 2: Japanese Patent Application "Kokai" No. 9-126744 (FIG. 13).

DISCLOSURE OF THE INVENTION

Problem to be Solved by Invention

In the case of the conventional surface defect inspection disclosed by Patent Documents 1 and 2, the irradiation unit for irradiating an inspection target surface irradiates a stripes-form lightness/darkness pattern on the painted surface. Hence, the wraparound of the irradiation light used for the surface inspection occurs only in the direction normal (transverse) to the stripes-form lightness/darkness pattern.

As a result, if the inspection target surface has a defect which is present along the direction of the stripes-form lightness/darkness pattern (the same direction as the extending direction of the stripes), it is difficult to detect such defect.

Further, with this technique, substantially only convex defect can be detected. And, it is difficult to obtain any lightness/darkness difference at the irradiated portion at the reflecting portion, thus tending to result in erroneous detection in the binarizing process. Also, it is difficult to detect a defect present on a design line or adjacent thereto.

Furthermore, as shown in FIGS. 17 and 18, as the irradiation axis of the irradiation light employed for the inspection intersects the imaging optical axis of the imaging camera, the amount of light which can be introduced into the imaging camera is insufficient. In this respect too, there is room for improvement.

Also, with such inspection system, due to its optical complexity, the process effected on the defect evaluation side is necessarily complicated. At the same time, precision is required in the positional relationship in the irradiation unit and the imaging unit.

The object of the present invention is to obtain a surface defect inspection technique in which the irradiation unit and the imaging unit have most rational and simple constructions possible and which yet is capable of reliable inspection.

Means to Achieve the Object

According to a surface defect inspecting method relating to the present invention, by irradiating an irradiation light having a predetermined pattern on an inspection target surface, imaging the surface irradiated with the irradiation light and inspecting the inspection target surface based on an obtained image of the inspection target surface, is characterized in that:

said irradiation light irradiated from an irradiation face has a mesh-like pattern including meshes of a same shape, each mesh having an irradiation area (area of the irradiating portion) smaller than a non-irradiation area (area of the portion appearing as a dark area) in a plane normal to the optical axis; and said inspection target surface is inspected, based on lightness/darkness information of an image area in the obtained image corresponding to a non-irradiated area in the inspection target surface.

With this method, from the irradiation face, there is irradiated an irradiation light having light portions distributed in a mesh pattern, with each light portion enclosing therein a dark portion (dark face).

When the inspection target surface irradiated with the above irradiation light is imaged by an imaging device such as a CCD camera, in case the inspection target surface is a flat surface with no defect present thereon, the mesh-like lightness/darkness pattern on the irradiation side will be imaged substantially as it is. Whereas, in case a defect is present e.g. immediately blow the dark portion, the light irradiated from the dark portion of the irradiation side will be bent in its optical path by the presence of the defect and enter an area (non-irradiated area) which should be a dark portion if it were not for the defect.

As a result, it is possible to form an isolated light point substantially at the center of the area, i.e. a dark portion, within the mesh.

The present invention enables defect detection by utilizing this phenomenon. And, as each mesh has a same "intra-mesh" shape, a defect which may be present within any mesh can be detected substantially under same condition.

Further, with this construction, the mesh corresponds to the irradiation area and the intra-mesh area corresponds to the non-irradiation area, thus securing a large non-irradiation area. Hence, the defect can be detected with high possibility as a light portion appearing in the dark portion.

Moreover, with the present invention, as the light portion is formed like a mesh, the wraparound light introduced along the entire perimeter surrounding the dark portion can enter a pixel at a predetermined position of the imaging device having a two-dimensional extension. Consequently, the invention makes it possible to defect having such a shape, a size or a depth which was difficult to be detected by the conventional technique.

In the study conducted by the present inventors, in case the mesh size had an average diameter (the diameter in case the mesh is considered as a circle) of 25 mm approximately, a defect which was substantially circular in its plan view and had a radius of 0.3 mm and a depth of 0.03 mm approximately could be discriminated by a standard CCD camera.

Also, as the inspection is effected normally with continuously moving the inspection target object relative to the surface defect inspecting apparatus, in association with this movement, some mesh can capture the defect as a distinct defect image, so that the detection can be done reliably.

Moreover, as the border line delimiting the light portion and the dark portion forms a mesh shape, in the detection of a defect such as "orange peel", it is possible to solve the problem of the conventional stripe-like pattern which has a particular directionality in the detection.

As a surface defect inspecting apparatus implementing such surface defect inspecting method as above, comprising an irradiating means for irradiating an irradiation light having a predetermined pattern on an inspection target surface; an imaging means for imaging the inspection target surface irradiated with the irradiation light; and an image processing mans for effecting an image processing on an image obtained by the imaging means; the apparatus can be constructed such that;

said irradiating means irradiates, from an irradiation face thereof, an irradiation light having a mesh-like pattern including meshes of a same shape, each mesh having an irradiation area smaller than a non-irradiation area in a plane normal to the optical axis; and said image processing means, in said image processing, is capable of processing lightness/darkness information of an image area in the obtained image corresponding to a non-irradiated area in the inspection target surface.

Incidentally, in the above-described method, if an image obtained when the irradiation light is irradiated on a normal inspection target surface is a normal obtained image and the brightness of the irradiation area in the normal obtained image is defined as a high brightness whereas the brightness of the non-irradiation area is defined as a low brightness; then, preferably, an intermediate brightness area which is present within the obtained image and which is an area of intermediate brightness between the high brightness and the low brightness is used as a target area in effecting the inspection.

As described above, with the present invention, defect detection is made possible by utilizing the wraparound of the light from the light portion of the lightness/darkness pattern, due mainly to the presence of the defect. Hence, the image of this defect has an intermediate brightness between the high brightness of the irradiation portion and the low brightness of the non-irradiation portion.

Therefore, with preclusion of the high brightness portion and the low brightness portion, it becomes readily possible to extract an area where the defect is present with high possibility. As a result, through simple image processing, an image area believed to be associated with the target defect can be extracted speedily.

The surface defect inspecting apparatus for carrying out such process, in case if an image obtained when the irradiation light is irradiated on a normal inspection target surface is a normal obtained image and the brightness of the irradiation area in the normal obtained image is defined as a high brightness whereas the brightness of the non-irradiation area is defined as a low brightness, can be accomplished by a construction wherein said image processing means includes an intermediate brightness area extracting means for extracting an intermediate brightness area which is present within the obtained image and which is an area of intermediate brightness between the high brightness and the low brightness.

Incidentally, the irradiation light employed by the surface defect inspecting method of the invention forms, in its irradiation face, the light portions as the irradiation side in the form of meshes and the dark portions within the respective meshes. Therefore, with this pattern, when the inspection target surface is a flat surface causing no distortion in the image of the meshes and also when the inspection target surface is a curved surface thus causing distortion in the image of the meshes, such effects are reflected also in the respective obtained images. Therefore, in the image processing, the normal portions of the meshes substantially unrelated to the defect can be precluded, as continuous light portions, from the target area.

That is, if the image area corresponding to the irradiation area in the inspection target surface is extracted as continuous light areas and these continuous light areas are precluded from the target area, the area apparently corresponding to the defect can be extracted easily.

For implementing such surface defect inspecting method, said image processing means can include a continuous light area extracting means for extracting continuous light area which is the image area corresponding to the irradiation area of the inspection target surface and a precluding means for precluding the extracted continuous light areas from the target area.

Further, in the surface defect inspecting method described above, preferably, the image area corresponding to the non-irradiation area of the inspection target surface is extracted for each enclosed dark area and if an isolated light area is present within said enclosed dark area, this isolated light area is determined as the target area.

With this method, considering the fact that the irradiation light forms a mesh-like pattern, the area within each mesh is recognized as a dark area which is basically enclosed and if an isolated light area is present within this dark area, this is judged as the possibility of presence of an abnormality (defect) in the inspection target surface and determined as the target area.

In this case, e.g. even when the inspection target surface is a curved surface so that there occurs relatively large distortion in the basic mesh-like pattern, effective defect detection can be carried out, by utilizing the shape characteristics of the irradiation light.

The surface defect inspecting apparatus using this surface defect inspecting method can implement the above-described surface defect inspecting method if said image processing means includes:

an enclosed dark area extracting means for extracting each enclosed dark area whish is the image area corresponding to the non-irradiation area of the inspection target surface; and an isolated light area extracting means for extracting an isolated light area present within said extracted enclosed dark area.

Further, preferably, said irradiation light of said irradiating means is formed by a plurality of light emitting elements distributed in a mesh-like pattern.

In this case, by using light emitting elements, it is possible to reduce the possibility of occurrence of detection failure of a small defect resulting from brightness shortage in case e.g. an indirect irradiation construction is employed. And, as sufficient brightness can be secured on the irradiation side, the inspection can be carried out with certainty and high reliability. Further, by appropriately changing the distribution of the light emitting elements, on a black plate, it is possible to obtain an irradiation light having a desired mesh-like pattern.

Further, as will be described later also, in the case of the present invention, the image is obtained with setting the focal point of the imaging device on the irradiation face (light emitting face) of the irradiation side. In this, as a large brightness difference can be obtained between the light emitting portion of the light emitting element and its background, a sharper image can be obtained on the imaging side. Hence, the image portion resulting from the defect, which image portion tends to be a small blurred image, can be caused to stand out easily.

On the other hand, it is also preferred that the irradiation light of the irradiating means is formed through transmission between narrow slits distributed in a mesh-like pattern. In this case, as conventionally practiced, a diffuser plate can be disposed forwardly of a light source and a shielding member for forming the dark portions congruent with the areas within the meshes can be disposed further forwardly. With this, it is readily possible to obtain an irradiation light suitable for the purpose of use of the invention and its border lines can be clear.

Further, in the technique described so far, preferably, the mesh size is adjustable.

In the case of utilizing the wraparound light due to a defect as in the case of the present invention, the imaging side requires that the optical path of the light reflected off the defect reach the light portion forming a mesh. Hence, whether such wraparound occurs or not is closely related to the size of the detection target defect (including its aperture area, depth, etc.) and the size of the mesh. Therefore, by rendering the mesh size adjustable, effective detection is made possible through appropriate selection of the size of the mesh which allows effective detection of a predetermined size of defect.

Further, preferably, the brightness difference between the irradiation area and the non-irradiation area in the inspection target surface is adjustable.

For instance, in case the inspection target is a painted surface of an automobile body, this surface includes some portions which can be considered as substantially flat surfaces and other portions which are curved surfaces. Therefore, there exist irregularities in the optical path distances in the irradiation unit and the imaging unit, hence, an amount of light required for defect detection cannot always be obtained under a good condition.

However, if the brightness difference is adjustable, it is readily possible to select an amount of light required for the wraparound, in accordance with each particular condition of the inspection target. So that, reliable detection is made possible.

In the foregoing discussion, there is no particular limit in the method of forming the irradiation light. With the present state of the art, however, in order to form the irradiation light forming a relatively complex pattern as employed in the present invention, it would be most realistic, in terms of the manufacture technique, to employ a number of light emitting elements distributed in a predetermined pattern.

Therefore, in the case of employing such construction, the surface defect inspecting apparatus for accomplishing the object of the present invention will be constructed as follows.

Namely, a surface inspecting apparatus relating to the present invention, comprising: a plurality of light emitting elements arranged in a predetermined layout pattern; an imaging camera for imaging an inspection target surface irradiated with an irradiation light of the light emitting elements; and an outputting portion for outputting the obtained image information of the imaging camera; characterized in that:

said layout pattern comprises a continuous arrangement of the light emitting elements so as to leave a dark face of a predetermined shape therewithin; and said imaging camera is disposed so as to receive, on at least one said dark face, the irradiation light of each light emitting element reflected off the inspection target surface.

With this surface defect inspecting apparatus too, its inspection principle utilizes the wraparound of the irradiation light. In the utilization of this inspection principle, the irradiation unit employs the continuous layout pattern of the light emitting elements arranged so as to leave a dark face of a predetermined shape therewithin.

With this construction, in case, e.g. the painted surface is a flat surface and the layout pattern of the light emitting elements in the irradiation unit is hexagonal, and the optical axis of the irradiation light and the optical axis of the imaging camera are directed along the normal line of the painted surface, if no defect is present in the painted surface, the obtained image will have a hexagonal lightness/darkness pattern. Whereas, if a defect is present, this defect will form an isolated light point in the dark face formed inside the hexagon as shown in FIG. 7. Therefore, the image associated with this defect can be captured reliably by the imaging camera.

Moreover, as the imaging camera is disposed at the dark face, it becomes possible to align the optical axis direction of the irradiation light with the optical axis direction of the imaging side, thus enabling an imaging inspection under the so-called "epi-illumination" condition.

And, if there is provided a defect evaluating portion for detecting a defect on the inspection target surface by evaluating an output signal from said outputting portion, a defective portion can be evaluated and extracted automatically, with utilizing the analytical technique established as the image processing technique.

Preferably, said layout pattern comprises a repetitive layout pattern which repeats itself along a predetermined direction.

With such repetitive pattern, the image processing on an obtained image can be carried out repeatedly on a same basis, e.g. with using the layout pattern portion of the light emitting elements and the dark face formed therewithin as one unit. Further, in case the inspection target surface is moving, a same inspection target surface portion can be inspected repeatedly, so that sufficient information for enhancing reliability can be obtained on this inspection target surface portion.

More preferably, there is provided a conveying mechanism for moving said inspection target surface along a direction relative to said plurality of light emitting elements and said imaging camera; and the direction of repetition of said layout pattern comprises said direction of relative movement.

With this type of surface defect inspection, the inspection can sometimes be effected with the inspection target surface being automatically moved. So, if a predetermined inspection target surface is imaged in repetition with the repetition of the predetermined layout pattern to obtain image information thereof, highly reliable inspection can be carried out.

Further, preferably, the light emitting face (irradiation face) of said plurality of light emitting elements and an imaging face of said imaging camera are present in a common plane.

With this type of inspection, the image brightness of the obtained image, the position of the image portion, etc. are influenced significantly by the positional relationship between the inspection target surface relative to the light emitting face and the imaging face. In this regard, if the light emitting face and the imaging face are present in a common plane, the imaging unit integrating these can be constructed easily. And, only with the adjustment of the distance from this common plane to the inspection target surface, the optical construction for the inspection can be substantially specified. Hence, the inspection reliability can be established from this respect also.

As described above, if the irradiation unit comprises a plurality of the layout patterns each comprising a continuous arrangement of the light emitting elements so as form a dark face of a predetermined shape therewithin, the image of the inspection target surface obtained through the imaging camera will include a number of light emitting images of the light emitting elements. And, in this, depending on such condition as the shape of the inspection target surface, there may occur discontinuity in the light emitting images of the light emitting elements arranged continuously, thus making it difficult to discriminate such discontinuity from a defect.

For solving such problem, according to the surface defect inspecting apparatus of the present invention, the apparatus comprises: an irradiation unit comprising a plurality of sets of layout patterns each including a plurality of light emitting elements continuously arranged so as to leave a dark face of a predetermined shape therewithin; an imaging camera for imaging an inspection target surface irradiated with irradiation light of said irradiation unit; and a defect evaluating means for evaluating an output signal from said imaging camera, thus detecting a defect present on said inspection target surface;

wherein said defect evaluating means includes an isolated point extracting portion for determining, as a defect candidate, a prominent brightness area isolated in a lightness/darkness image of said inspection target surface generated from said output signal, and a defect candidate discriminating portion operable to preclude, from the defect candidates, a defect candidate contained within an area indicative of light emitting images of the continuously arranged light emitting elements in the lightness/darkness image.

With this construction, on a defect present within the irradiation points of the light emitting elements continuously arranged substantially in a mesh-like pattern (typically in the form of a ring), that is, on the inspection target surface opposed to the dark face, a portion of the irradiation lights will impinge from the entire periphery of this defect, so that the image of the defect will appear light prominently in the dark face image. Hence, a defect candidate can be detected as a prominent brightness area isolated in the lightness/darkness image. Further, in the respect of the detection problem that a discontinuity in the light emitting images of the continuously arranged light emitting elements too may be erroneously detected as an isolated prominent brightness area (referred to also as "isolated point"), such erroneous defect detection is reduced, by precluding from the defect candidates, any isolated point present on an extension line of the continuous series of light emitting images in the predetermined pattern.

As the inspection target surface is moved relative to the imaging camera or the irradiation unit, a defect will necessarily deviate from the irradiation points of the group of the light emitting elements and come eventually to the position opposed to the dark face. Therefore, there will occur no problem if the area of the continuous light emitting images as the prominent brightness area detected in the predetermined pattern is precluded from the defect candidate.

Because of the use of the irradiation unit comprising the series of many light emitting elements, the reflection lights from the light emitting elements off the inspection target surface will be captured by the imaging camera and these will appear as light emitting images in the image outputted from the imaging camera. However, the brightness value of this light emitting image may vary, depending on the inspection condition, especially, on the condition of the inspection target surface.

In the present invention, this brightness value of the light emitting image constitutes an important reference for the defect judgment. Then, in order to compensate for such variation as above, advantageously, there is provided a preprocessing portion for effecting an image processing such that the brightness level of the continuous light emitting image area in an actual inspection may agree substantially with the brightness level of the light emitting image of the continuously arranged light emitting elements obtained from a normal inspection target surface, said latter brightness level being employed as a reference for generating the lightness/darkness image from the output signal of the imaging camera. Effecting such brightness adjustment for achieving agreement with the reference brightness level of the light emitting image obtained for the inspection target surface in advance on the obtained image can contribute to improvement in the precision in the subsequent defect determination.

In case e.g. the inspection target surface is smaller than the imaging filed of the imaging camera, an object (e.g. background) other than the inspection target surface may be included in the obtained image. In this regard, as position information of such unnecessary image area can be foreseen or can be grasped by the well-known background selecting algorithm, then, in the present invention, it is proposed to effect a masking operation on an area integrating a peripheral area including the prominent brightness area precluded from the defect candidate described above, together with an unnecessary image area such as a background, as a defect determination non-target area, relative to the obtained image.

Further and other features and advantages of the invention will become apparent upon reading the following description of the embodiments with reference to the accompanying drawings.

EFFECT OF THE INVENTION

It has become possible to reliably detect such a defect in e.g. a painted surface of an automobile body, detection of which was difficult with the conventional technique.

BEST MODE OF EMBODYING THE INVENTION

Next, a surface defect inspecting apparatus 100 relating to the invention will be described.

The surface defect inspecting apparatus 100 of the invention is for use in an inspecting system 200 shown in FIG. 1 which corresponds to FIG. 17. FIG. 1 shows the entire construction of the inspecting system 200 and FIGS. 2 and 3 show the entire construction of the surface defecting apparatus 100. FIG. 4 shows the construction of an imaging unit 300 of the surface defect inspecting apparatus 100. FIG. 5 shows the construction of an evaluating section for obtained image information.

This inspecting system 200 too, as described in the prior art section, is provided for surface defect inspection of bumpers 1 for example. In this system 200, the surface defect inspecting apparatus 100 is disposed downstream a stock station 202 and upstream a visual inspecting station 203. This surface defect inspecting apparatus 100 includes an imaging unit 300 having the unique construction of the invention.

By effecting a copying operation along the outer contour of the bumper 1, this imaging unit 300 is capable of effecting the inspection with much higher precision and reliability than the conventional art.

Next, the construction of the inspecting system 200, the copying construction of the imaging unit 300 of the surface defect inspecting apparatus 100 and the processing of obtained images will be described in details in the mentioned order.

[Inspecting System]

As shown in FIG. 1, in the inspecting system 200 relating to the present invention, a moving path of the bumper 1 as an inspection target by a conveying robot 2 is formed as a straight moving path.

In FIG. 1, the inspection target bumper 1 is conveyed from the right upper side to the left lower side in the figure. As shown, the inspection is done on a pair of bumpers 1 as one unit for inspection. Therefore, along this conveying direction, there are disposed the stock station 202, the surface defect inspecting apparatus 100, and the visual inspecting station 203.

The movement of the bumpers 1 from the stock station 202 to the conveying robot (an example of "conveying mechanism") 2 is done by a charging worker 204 and a visual inspection is done by an inspecting worker 201. These respects are the same as the conventional art.

Referring to the process in accordance with the flow thereof, the charging worker 204 takes out, when needed, the pair of bumpers 1 from the stock station 202 and sets these to a bumper support portion 2a of the conveying robot 2.

The conveying robot 2, while holding the bumpers 1, moves along the conveying path to the downstream side. In this, there takes place no change in the postures of the bumpers 1 and the bumpers 1 just move in juxtaposition along the conveying path. When the bumpers 1 enter the surface defect inspecting apparatus 100, the imaging unit 300 moves with change in its posture to copy the surface contour of the bumper 1. In this movement, as will be described later, an irradiation unit 3 of the imaging unit 300 is maintained in parallel with the inspection target surface and the optical axis of an imaging camera 4 is maintained along the normal line to the inspection target surface, thereby maintaining constant the distance between the inspection target surface and the imaging unit 300.

And, lightness/darkness pattern of the irradiation light reflected off the bumper 1 is imaged by a plurality of imaging cameras 4 included in the imaging unit 300. The result of this imaging operation is sent to a defect evaluating portion 6 constituting a defect evaluating means as the analyzing side, whereby evaluation of e.g. presence/absence of a defect is effected.

The inspecting worker 201 positioned on the conveying-wise downstream side is to effect visual inspection of the bumpers 1 sent. As shown in FIG. 1, at this timing, the inspecting worker 201 has obtained, on an inspection result projector 15, the evaluation information from the defect evaluating portion 6 as information of a portion which should be taken notice of in the inspection. Hence, the worker can proceed in this visual inspection with placing emphasis on that portion in particular.

[Copying Construction of Imaging Unit of Surface Defect Inspecting Apparatus]

a. Imaging Unit 300

FIG. 4 shows the imaging unit 300 in a plan view (a), a front view (b) and details thereof (c), respectively. As shown, the imaging unit 300 consists basically of a unit frame 300a having a substantially rectangular solid shape and pivotal support frame portions 300b provided at opposed ends of the unit frame 300a and vertically extending therefrom.

As shown also in the figures, the upper end face of the unit frame 300a is constructed as what is referred to as the irradiation unit 3 herein. This irradiation unit 3 includes a number of light emitting elements 30 arranged in repeated layouts of hexagonal units.

Further, at the width-wise center of this irradiation unit 3, there are provided lens faces 4a (i.e. imaging portions) of the imaging cameras 4 disposed by a predetermined equal interval. In the illustrated example, total of 10 (ten) imaging cameras 4 are provided. As shown in FIG. 4(b), inside the unit frame 300a, there are provided DC power sources 300c for the imaging cameras 4 and the light emitting elements 30.

b Copying Construction

The above-described imaging unit 300 is adapted to be supported by a pair of right and left support shafts 300d provided at the leading end of the pivot support frame portions 300b. Each support shaft 300d is rotatable about its own axis and is movable in the vertical direction and in the fore and aft direction relative to an apparatus frame 100a of the surface defect inspecting apparatus 100.

FIG. 2 is a view showing the apparatus frame 100a as seen from its front side extending normal to the conveying path. In this figure, the conveying robot 2 is moved from the right side to the left side.

FIG. 3 is a view showing the apparatus frame 100a as seen from the incoming side (i.e. the side face) of the conveying robot 2.

As shown in FIG. 2, the apparatus frame 100a is a structure which has a portal shape in its side view and has a rectangular shape in its front view.

A traveling frame 100b is provided to be movable along the right/left direction (the direction along the conveying direction) relative to the apparatus frame 100a in its front view and there is provided a vertical moving frame 100c which is vertically movable relative to the same.

This vertically movable or lift frame 100c is movable along the vertical direction along a rail (rc) provided in the traveling frame 100b. This vertical movement is effected by a lift motor Mc provided at a center portion of the traveling frame 100b.

The movement of the traveling frame 100b along the conveying direction is effected by a rail (rb) allowing the traveling of this traveling frame 100b and a drive transmitting mechanism which transmits traveling drive force from a traveling motor Mb provided in the apparatus frame 100a to the traveling frame 100b.

Further, as shown in FIG. 3, for the pair of right and left support shafts 300d attached to the leading ends of the pivot support frames 300b, there are provided a rotary motor Md and a gear transmission mechanism G for transmitting the rotation of this rotary motor Md in a reduced speed to the support shafts. In association with the rotation of the rotary motor Md, the pivotal posture of the imaging unit 300 can be adjusted.

Incidentally, a laser sensor 400 is provided for detecting the current position and inclination (inclination shown in FIG. 2) of a surface portion of the bumper 1 which is to be inspected by the imaging unit 300 (see FIG. 1).

Information from this laser sensor 400 is sent to a host computer 14 having a function of a copying control device also.

In this computer 14, there are generated control commands based on the shape information of the bumpers 1 and the conveying position information of the conveying robot 2. In this, the control information is corrected based on the detection information from the laser sensor 400, thus sending control information to the above-described lift motor Mc, the traveling motor Mb, and the rotary motor Md, respectively, thus effecting an automatic control for causing the imaging unit 300 to have an appropriate positional relationship relative to the inspection target surface.

This appropriate positional relationship, as shown in FIG. 2 is a relationship wherein the optical axis of the imaging camera 4 extends along the normal direction to the inspection target surface, the irradiating face (light emitting face 3a) extends parallel with the inspection target surface and both the irradiating face (light emitting face 3a) and the imaging face (i.e. the lens face 4a) are located at a predetermined distance from the inspection target surface. FIG. 2 schematically shows two different positions and postures of the imaging unit 300 relative to the inspection target surface.

[Processing of Obtained Image]

With the surface defect inspecting apparatus 1 relating to the present invention, as shown in FIG. 4 and FIG. 5, the principal system for the imaging inspection, as described above, comprises the irradiation unit 3 for irradiating an irradiation light to the painted surface of the bumper 1 as the inspection target surface, the imaging cameras 4 for picking up the image of the inspection target surface irradiated by the irradiation unit 3, and an image processing controller 5 for effecting evaluation of presence/absence of a defect on the inspection target surface by using output signals from the imaging cameras 4 and outputting the defect evaluation result.

As shown in FIGS. 4 and 5, this controller 5 is provided a lower computer relative to above-described host computer 14 and includes a monitor 12 and a printer 13 as output devices to be connected to an output portion 10 of this image processing controller 5 per se.

The image processing controller 5 includes an irradiation/imaging controlling portion 9 for controlling the irradiation unit 3, an image inputting portion 7 for inputting output signals from the imaging cameras 4 and converting them into digital image data (referred to simply as "input image" hereinafter) and mapping the data in a memory 8, and a defect evaluating portion 6 for effecting defect evaluation using the input image.

Further, the image processing controller 5 is connected to the host computer 14 via a communicating portion 11 so as to transmit the data thereto.

This host computer 14 stores therein information of the bumpers 1 as the inspection target which is downloaded, when necessary, to the image processing controller 5 and movement information of the conveying robot 2 as the conveying device. Further, defect information of the painted surface generated at the image processing controller 5 is also uploaded from the image processing controller 5 to the host computer 14 to be stored therein.

The visual inspecting station includes the inspection result projector 15 and the printer which are controlled via terminals connected in a network with the host computer 14. So that, based on the defect information transmitted from the image processing controller 5 to the host computer 14, the position of the defect, etc. is indicated through the inspection result projector 15 to the inspecting worker.

As described above, the imaging unit 300 is controlled such that the light emitting face 3a of the irradiation unit 3 and the lens face (corresponding to the imaging face) 4a of the imaging camera 4 are placed in opposition to the inspection target surface of the bumper 1 as being conveyed by the conveying robot 2 and the normal lines of the irradiating face 3a and the imaging face 4a are aligned with the normal line of the inspection target surface and the distance therebetween is kept constant.

As shown in FIG. 4, the irradiation unit 3 includes a number of light emitting elements (these will be referred to as LED elements hereinafter since LED elements are employed in the instant embodiment) 30 which are arranged in a mesh-like layout pattern leaving hexagonal spaces and with repetition of this hexagonal layout patterns continuously (with reduced distance between adjacent LED elements 30). The space formed within the LED elements 30 arranged in the hexagonal mesh pattern is referred to herein as "a dark face 31" which actually is a black or dark-colored plate face.

With the LED elements 30 arranged in the mesh-like pattern, there are formed many dark faces 31. And, at the dark faces 31 distributed uniformly along the inner center axis, the lens faces 4a of the imaging cameras 4 are arranged. In this way, the plurality of imaging cameras 4 are incorporated in the irradiation unit 3. For use, the focal point of the imaging camera 4 will be aligned not with the painted surface, but with the irradiating face 3a of the irradiation unit 3.

The image processing controller 5 includes a CPU as a core component thereof and functional portions for effecting various operations of the surface defect inspecting apparatus 100 which are realized in the form of hardware and/or software.

As shown in FIG. 6, as the functional portion relating particularly to the present invention, the defect evaluation portion 6 can be divided into a preprocessing portion 60A acting as an image processing means for converting the input image mapped in the memory 8 to a form suitable for defect detection and a defect determining portion 60B for detecting a defect on the inspection target surface by using the preprocessed input image.

The preprocessing portion 60A consists of a brightness adjusting portion 61 for effecting brightness adjustment on the input image and a binarizing portion 62 for effecting a binarizing operation on the brightness-adjusted input image. The brightness adjusting portion 61 employed in this embodiment is adapted to effect not only a gamma adjustment, but also brightness adjustment by a pixel area unit so that the brightness level of a light emitting image included in the input image may reach a brightness level of the light emitting image of the LED element obtained from a normal inspection target surface used as a reference for each paint color or paint face.

Further, the binarizing portion 62 includes a binarizing threshold determining portion 62a for determining a binarizing threshold value by a statistical technique from the lightness/darkness histogram of the input image and an image characteristics extracting portion 62b for effecting a smoothing operation on the input image for noise elimination and effecting also an edge enhancing filtering operation such as a Sobel filtering in order to enhance the contour of the light emitting image or the defect image. In operation, by using the binarizing threshold value determined by the binarizing threshold determining portion 62a, the input image which has been enhanced by the image characteristics extracting portion 62b is converted into a binarized image.

One example of input image binarized by the binarizing portion 62 is shown in FIG. 7. In this binarized lightness/darkness image, areas of high brightness are shown in white and the group of LED elements, i.e. the light emitting images, continuously arranged in the hexagonal layout pattern are shown as continuous hexagonal white contour lines. Whereas, the painted areas opposed to the dark faces 31 are shown as dark areas. And, a paint defect which may be present is shown as an isolated white area floating in the dark area, due to diffusion reflection of the irradiation light from around it.

Hence, the defect detection can be done by searching an area which is present in an area of prominent brightness (a white area in this embodiment) in a binarized image and which is not continuous in the predetermined pattern, i.e. by searching an isolated point. An image processing algorithm for searching a series of pixels having predetermined brightness values (density values) or searching an isolated area, can be an algorithm which per se is well-known.

However, due to e.g. variation in the reflection characteristics of the shape of the inspection target surface, which is a painted surface in this case, relative to the irradiation light, as shown in enlargement in FIG. 8, there can occur discontinuity in the light emitting images of the LED elements 30 which should appear properly as a continuous line, and such discontinuous portion can be detected as a defect erroneously. In order to effectively avoid such erroneous detection, the defect determining portion 60B is comprised substantially of a program.

That is, this defect determining portion 60B includes a defect candidate extracting portion 63 for detecting a non-continuous isolated pixel area comprised of a number of pixels within a predetermined number, as a defect candidate, a defect candidate discriminating portion 64 for precluding from the defect candidate, a defect candidate contained in an area showing the light emitting images of the continuously arranged LED elements 30 (the means for extracting this area is a continuous light area extracting means), an image mask generating portion 65 for effecting a masking operation by determining the isolated point area precluded from the defect candidate by the defect candidate discriminating portion 64 together with an unnecessary image areas such as a background as defect determination non-target area, a label setting portion 66 for effecting a labeling operation for assigning different labels (numbers) to different defect candidate areas in order to discriminate a plurality of defect candidate areas from each other, an area calculating portion 67 for calculating an area of each labeled defect candidate area, a defect judging portion 68 for determining a defect candidate as a real defect based on an area information from this area calculating portion 67 and writing this in a defect map. In this way, the defect determining portion consists of what are referred to herein as "an enclosed dark area extracting means" and "an isolated light area extracting means".

The defect candidate discriminating portion 64 includes a defect candidate chronological judging portion 64a for preventing detection as a defect candidate, a light area which occurs accidentally, by checking whether the area has been extracted as a defect candidate for a predetermined number of times based on images sent one after another from the imaging cameras 4, in order to discriminate the defect candidate extracted by the defect candidate extracting portion 63, and a light emitting image discontinuity searching portion 64b for preventing a discontinuity in the light emitting images from being recognized as a defect candidate by checking whether an extracted defect candidate (isolated point) is located on an extension line of continuous light emitting images.

The search for this discontinuity in the light emitting images can be effected by e.g. a shape characteristics extracting algorithm for extracting a dark area located on an extension line area at an interrupted end of the continuous light emitting image pixels while scanning these pixels. And, an isolated point located at such interrupted area will be precluded from the defect candidates.

Next, the process of defect valuation on a painted surface by the defect evaluating means 6 having the above-described construction will be explained with reference to the flowchart of FIG. 9.

First, each of frame images sent one after another from the imaging cameras 4 via the image inputting portion 7 is inputted to the memory 8 (#01). This inputted input image is subjected to the brightness (density value) adjustment by the brightness adjusting portion 61 (#02). For this, the characteristics amount of the input image is needed. Preferably, for obtaining this characteristics amount, the input image is divided into a predetermined number of blocks and a maximum value of density average values calculated for the respective blocks is used as the characteristics amount.

This characteristics amount can be utilized also for adjustment of opening degrees of the lenses of the imaging cameras 4. The binarizing threshold determining portion 62a determines a binarizing threshold value (#03) and the image characteristics extracting portion 62b effects the smoothing operation and the edge enhancing operation on the image (#04). Then, this input image is binarized into a binarized image (#05).

From this binarized input image, the defect candidate extracting portion 63 extracts, as a defect candidate, an isolated light pixel area from the predetermined number (this will be determined in advance according to e.g. image resolution) of pixels (#06).

From these extracted defect candidates, a defect candidate which belongs in the isolated points which occur momentarily or locally due to external light disturbance or the like are precluded therefrom (#07) and from these extracted defect candidates, a defect candidate belonging in an isolated point located at an interrupted area of the light emitting images is precluded from the defect candidates by the light emitting image discontinuity searching portion 64b (#08).

The peripheral area including the interrupted area of light emitting images discovered by the light emitting image discontinuity searching portion 64b is subjected, as an unnecessary pixel area, to a masking operation by the image mask generating portion 65, together with the background area other than the painted surface as the inspection target surface, determined based on the shape information of the bumper 1 as the inspection target object and the conveying position information of the conveying robot 2 which are transmitted from the host computer 14 (#09).

Incidentally, in this embodiment, in the conveying position information obtained from the host computer 14, the position of the mask is adjusted by checking in realtime any displacement of the bumper 1 by using e.g. a laser sensor, because the information may differ from the actual position (#10).

In this way, after the selection of defect candidates and elimination of the background image, the remaining defect candidates (isolated points) are labeled respectively (#11) and the area of each labeled isolated point is calculated (#12). Then, the process determines only an isolated point satisfying the predetermined area condition (whether it has an area greater than the threshold value or not) as a true defect (#13), and its coordinate positions, size, etc. are written into the defect map (#14).

[Post-Processing]

The above complete the process of defect evaluation on the painted surface by the defect evaluating means 6. Upon completion of the inspection of the painted surface through this process, in the visual inspecting station 203, there is effected a defect verification using the defect map provided with an ID agreeing with an ID of the bumper introduced to the visual inspecting station 203, included in the defect maps sent from the image processing controller 5 via the host computer 14.

In the course of the above, in order to facilitate the verifying operation by the inspecting worker, preferably, the inspection result projector 15 may be operated so as to indicate the defect portion based on the subject defect map. Needless to say, the defect information based on such defect map can be outputted on a paper sheet by the printer 13 connected to the outputting portion 10 of the surface defect inspecting apparatus 100 and this outputted paper sheet can be affixed to the bumper 1.

In the foregoing embodiment, the irradiation unit 3 includes the group of LED elements continuously arranged in the hexagonal mesh-like pattern. The shape of the mesh can be other than hexagonal. Further, the light emitting elements 30 can be other than LED elements.

Other Embodiments

Next, other embodiments of the invention will be described.

1. In the foregoing embodiment, a painted surface of an automobile body (in particular, a bumper) is inspected as an example. Instead, the inspection target can be any other inspection target surface having a surface defect. An example of this type is surface inspection of a press-formed article.

2. In the foregoing embodiment, the irradiation unit of the surface defect inspecting apparatus relating to the present invention includes a number of light emitting elements arranged so as to form a dark face therewithin. Instead of employing this construction, the irradiation unit may be constructed such that diffused lights from the rear side are caused to pass mesh-like slits.

An example of this further construction is shown in FIG. 10. In the case of the example shown in this figure, an irradiation box 112 accommodates therein a plurality of fluorescent tubes 111 and at its front face portion, there is provided a diffuser plate 113. Further, before this diffuser plate 113, there is provided a slit plate 114 for forming slits and a dark face therewithin, thus forming an irradiation unit suitable for the purpose of the present invention.

3. In all of the foregoing examples, the dark face is formed circular. Instead, the dark face can be constructed variously. (a) shows an example of square dark faces. (b) shows an example of oval faces oblong sideways. (c) shows an example of dark faces arranged in a staggered pattern relative to those shown in (a). (d) shows an example of dark faces of a small triangular shape.

The construction shown in (a) is suitable in case the imaging of the defect occurs substantially in the right/left direction and in the vertical direction. Whereas, the construction shown in (b) is preferred to be employed in case the inspection target surface is a curved surface so that vertically elongated dark faces will be formed on the imaging side. The construction shown in (c) is effective in case the defect tends to be formed continuously in the vertical direction and such vertically continuous defect can be detected by either one of the upper and lower two stages of the squares arranged in the staggered pattern. Further, in the case of (d), a relatively small defect can be easily detected.

4. In the foregoing embodiment, there is described the hexagonal layout pattern as the layout pattern of the light emitting elements. However, for the purpose of securing an uniform amount of light at the center of the dark face, a nearly circular layout pattern is preferred. And, FIG. 12 shows an example of octagonal pattern.

Further, in the case of this example, as shown in FIG. 13, there exist disposing portions where the light emitting elements are overlapped as indicated by (s) in the right/left direction which is the moving direction of the inspection target surface. Hence, when this construction is employed, there can occur a problem in defect detection along a path A, compared with a path B. Then, in this case, as shown in FIG. 14, preferably, no portions s1, s2 of the layout pattern of the light emitting elements have any overlapping portions relative to the moving direction (paths C, D) of the inspection target surface.

5. In the foregoing embodiment, the defect extraction is effected via the binarizing process. Instead, this can be done, based on ternarizing operation.

The condition of the image processing based on such ternarizing operation is illustrated in FIG. 15.

FIG. 15 shows (a) an original image, (b) an image after the ternarizing operation and (c) the image after precluding operation, respectively. In (a), the white portions denote portions C1, C3 having brightness and the shaded portion C2 denotes a dark defect portion. In (b), the portions having the intermediate gradation in (a) are shown as shaded portions. In (c), a target portion is shown as a shaded portion C3.

These images show a case when a defect is present in a painted portion corresponding to the dark face located at the second row, second column from the left upper end. The other portions show normal condition.

The obtained image, as shown in (a), consists of the portion C1 having high brightness K1 corresponding to the light portion on the irradiation side and the portion C2 having low brightness K2 corresponding to the dark portion.

And, when the intermediate brightness K3 portions are extracted, then, the ring-like portions C4 having intermediate brightness K3 and a defect-associated portion C3 having the intermediate brightness K3 can be extracted.

Then, by effecting expanding/contracting operation on the above, the ring-like intermediate brightness portions which are actually relatively small areas can be erased (shown at (c)), as a result, the defect-associated portion alone can be allowed to remain.

6. In the foregoing embodiment, the inspection target surface was described as a flat surface. In the case of a curved surface, such a pattern as forms, on the imaging side, a dark face shape suitable for predetermined detection is preferred. FIG. 16 shows such example.

As described hereinbefore also, in case the inspection target surface is a curved surface, there occurs such phenomenon as distortion of the mesh in a particular direction. FIG. 16(b) shows that in the case of irradiation of a ring-shaped irradiation light and the inspection target surface having a center axis along the lateral direction of the plane of the figure, an oval spectacles-like rings contracted in the vertical direction of the image is formed.

The occurrence of this type of distortion can interfere with the technique of the present invention which relies on formation of an isolated light area within a ring-shaped light area and extraction thereof as a defect image.

Therefore, in case the inspection target surface is a curved surface, it is preferred that the mesh-like distribution of the irradiation light from the irradiation face corresponding to the curved surface shape of the inspection target surface be set as a circular or a regular polygonal mesh-like pattern in the obtained image.

For instance, as shown in FIG. 16(c), in case a curved surface causing contraction in the vertical direction in the image is to be coped with, the mesh pattern should be set as vertically elongate mesh pattern, taking this contraction into consideration in advance.

With this, in the obtained image, within the portion recognized as a continuous light portion, the dark portion corresponding to the inside of the mesh can secure an area larger than a predetermined area. And, in case an intermediate brightness area is formed within the mesh due to presence of a defect, this can be formed as an isolated area. Hence, by implementing the method of the present invention, effective detection can be carried out.

The foregoing embodiment described the example of the inspecting system 200 which includes the stock station 202, the surface defect inspecting apparatus 100, and the visual inspecting station 203 disposed in the mentioned order. However, if this system is constructed as a manufacturing/inspecting system involving a predetermined surface work (painting, pressing, etc.), the stock station, the working section for effecting painting or the like, the surface defect inspecting apparatus and the visual inspecting station will be disposed in this order.

In the foregoing embodiment, the light emitting face of the light emitting elements and the imaging face of the imaging camera are disposed in a common plane. Instead, these faces may be disposed at positions of different distances from the inspection target surface.

INDUSTRIAL APPLICABILITY

There has been obtained a surface defect detecting apparatus capable of reliably detecting a small paint defect.

BRIEF DESCRIPTION OF THE DRAWINGS

[FIG. 15] an explanatory view showing defect extraction situation in case a ternarizing operation is effected,

[FIG. 16] an explanatory view of a preferred arrangement of light emitting elements in case the inspection target surface is a curved surface,

DESCRIPTION OF REFERENCE MARKS

Figure 1:
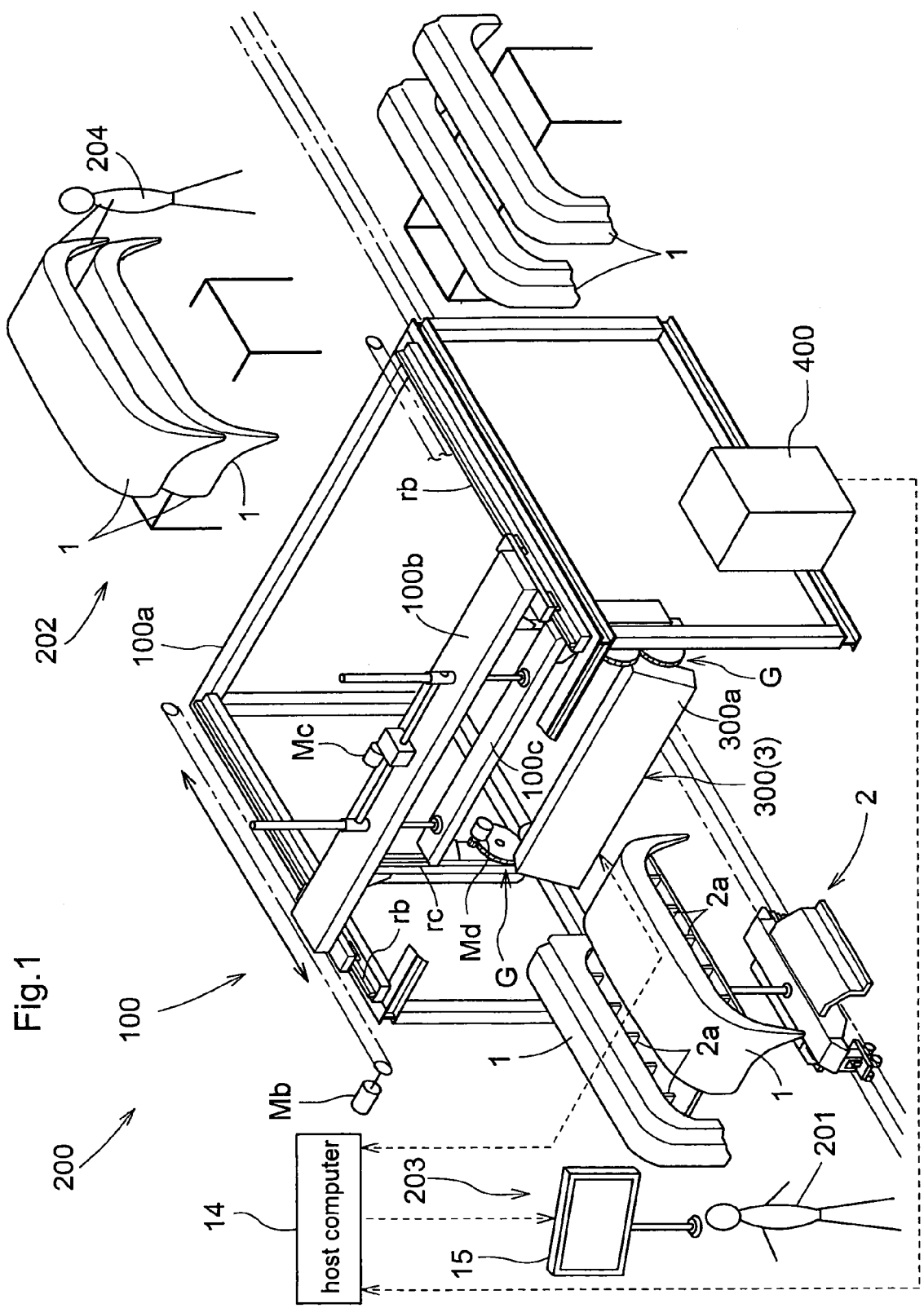
[FIG. 1] a view showing the schematic construction of an inspecting system using a surface defect inspecting apparatus relating to the present invention.
Figure 2:
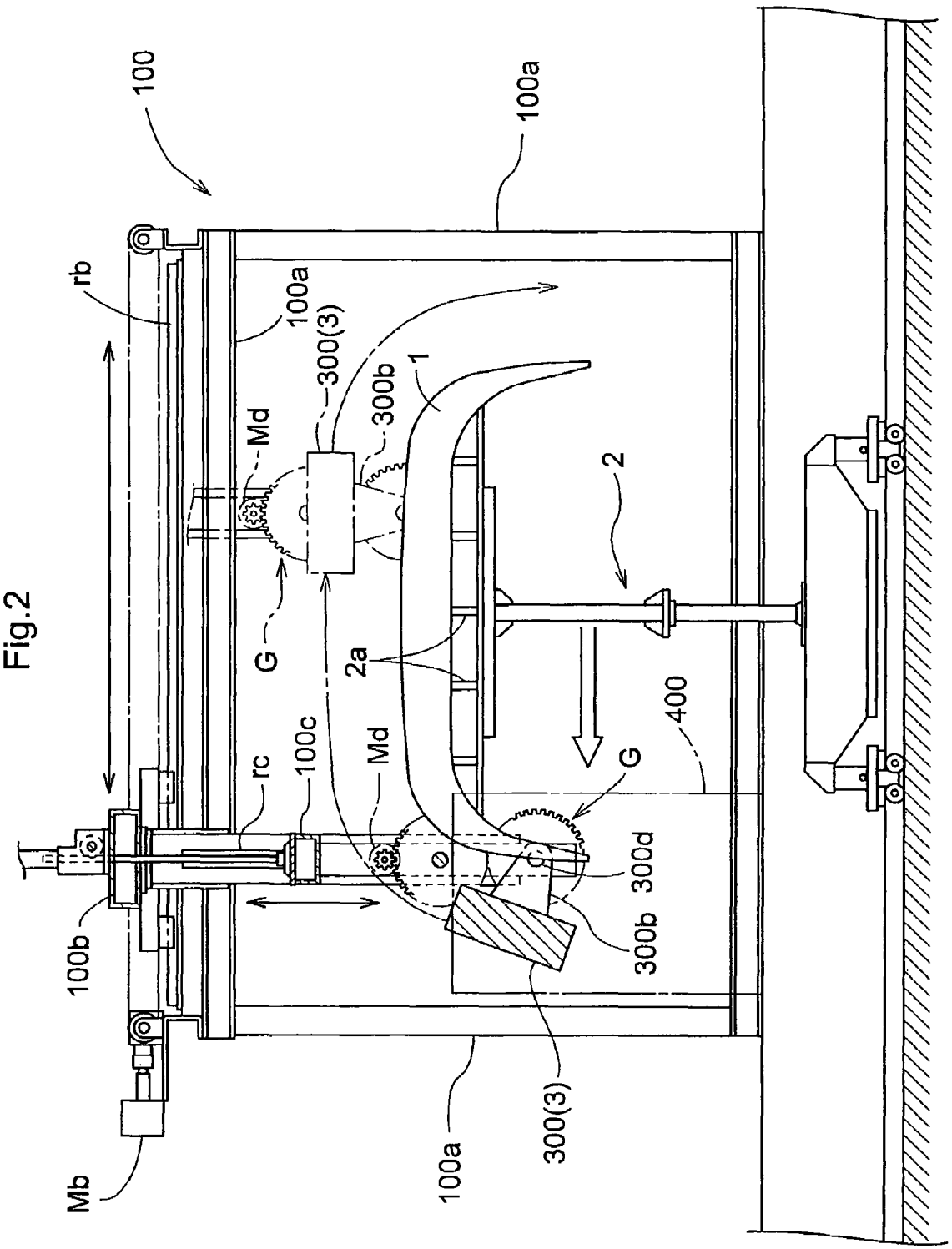
[FIG. 2] a view showing the schematic overall construction of the surface defect inspecting apparatus relating to the present invention.
Figure 3:
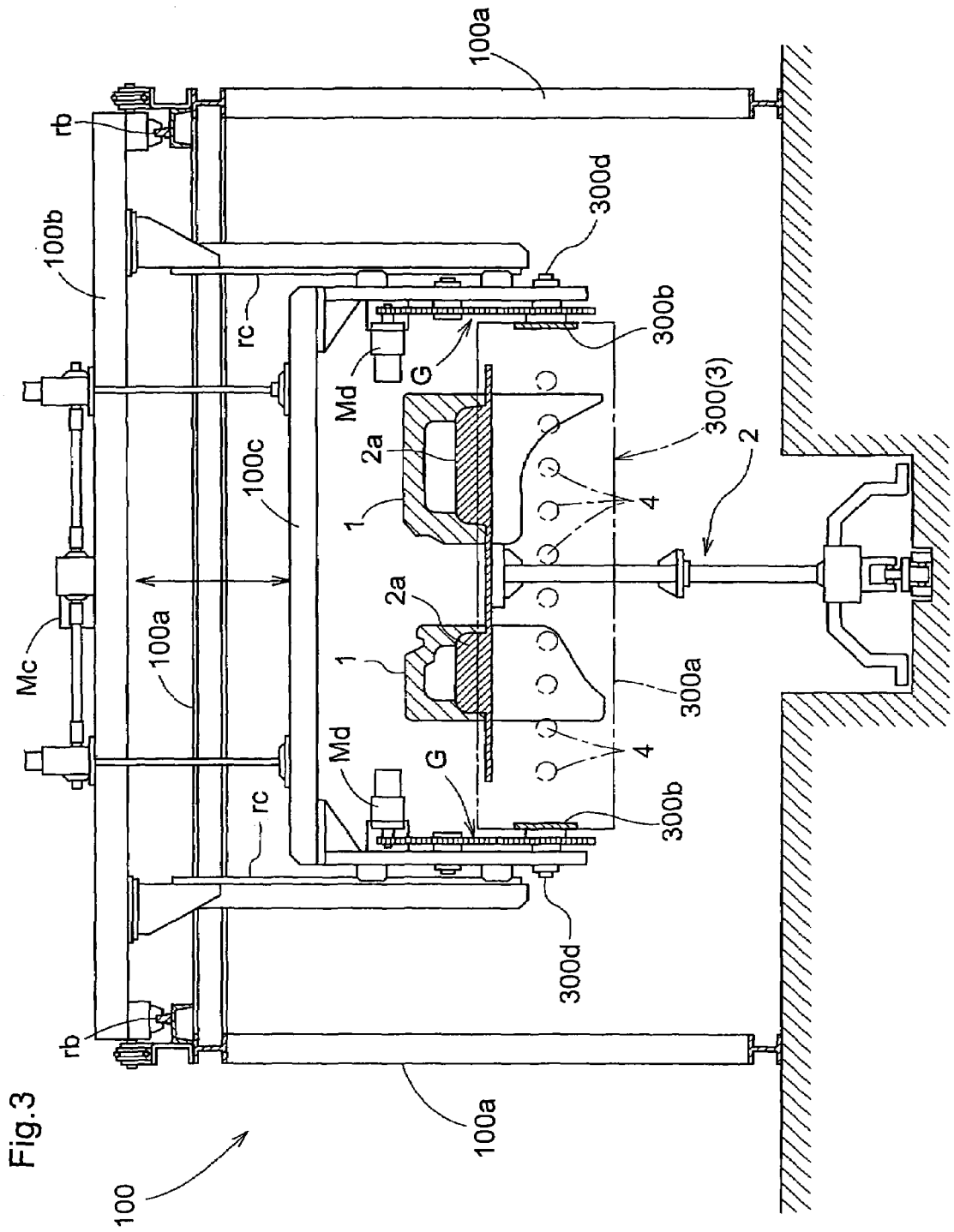
[FIG. 3] a view showing the schematic overall construction of the surface defect inspecting apparatus relating to the present invention.
Figure 4:
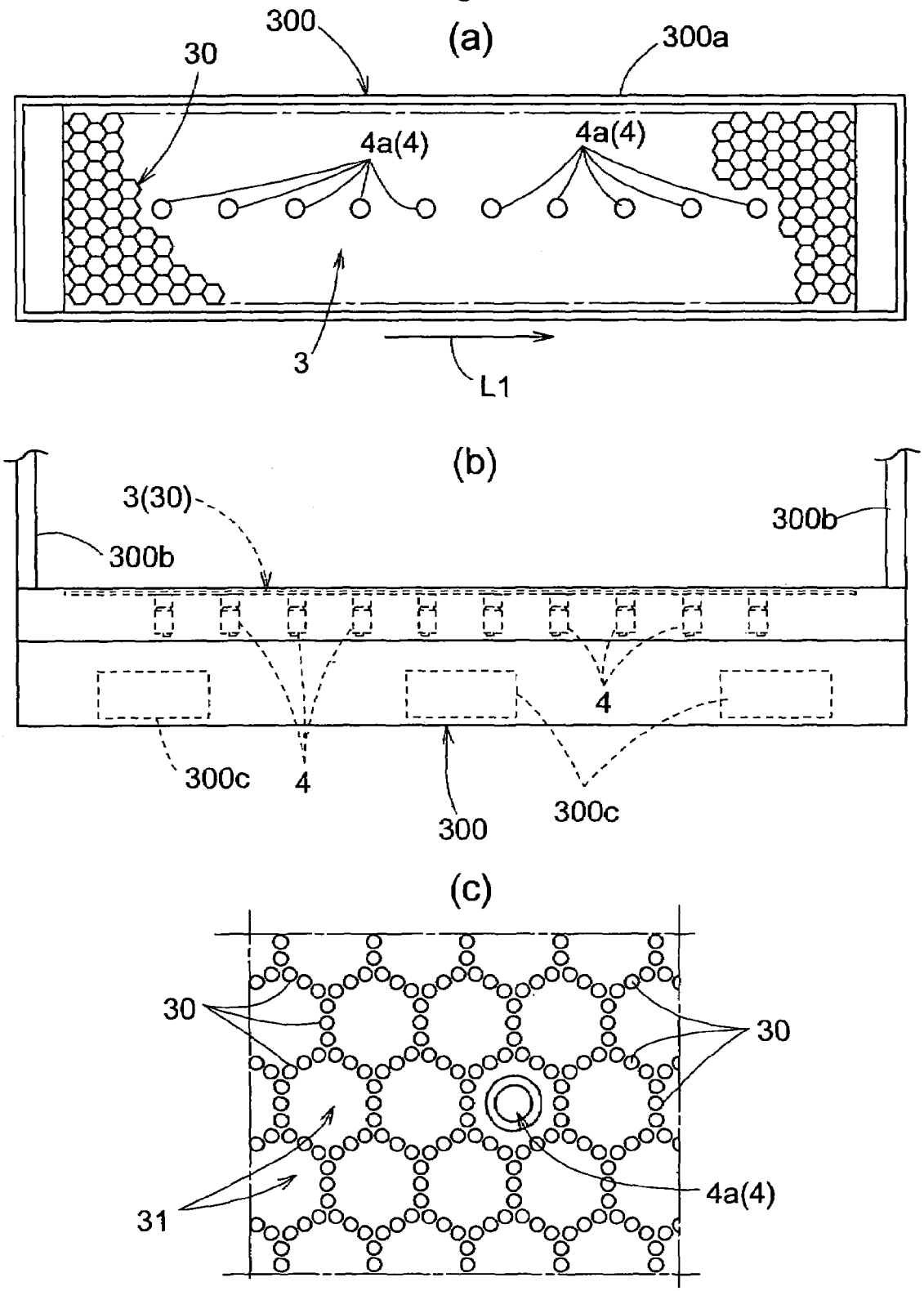
[FIG. 4] a view showing an imaging unit of the surface defect inspecting apparatus relating to the present invention.
Figure 5:
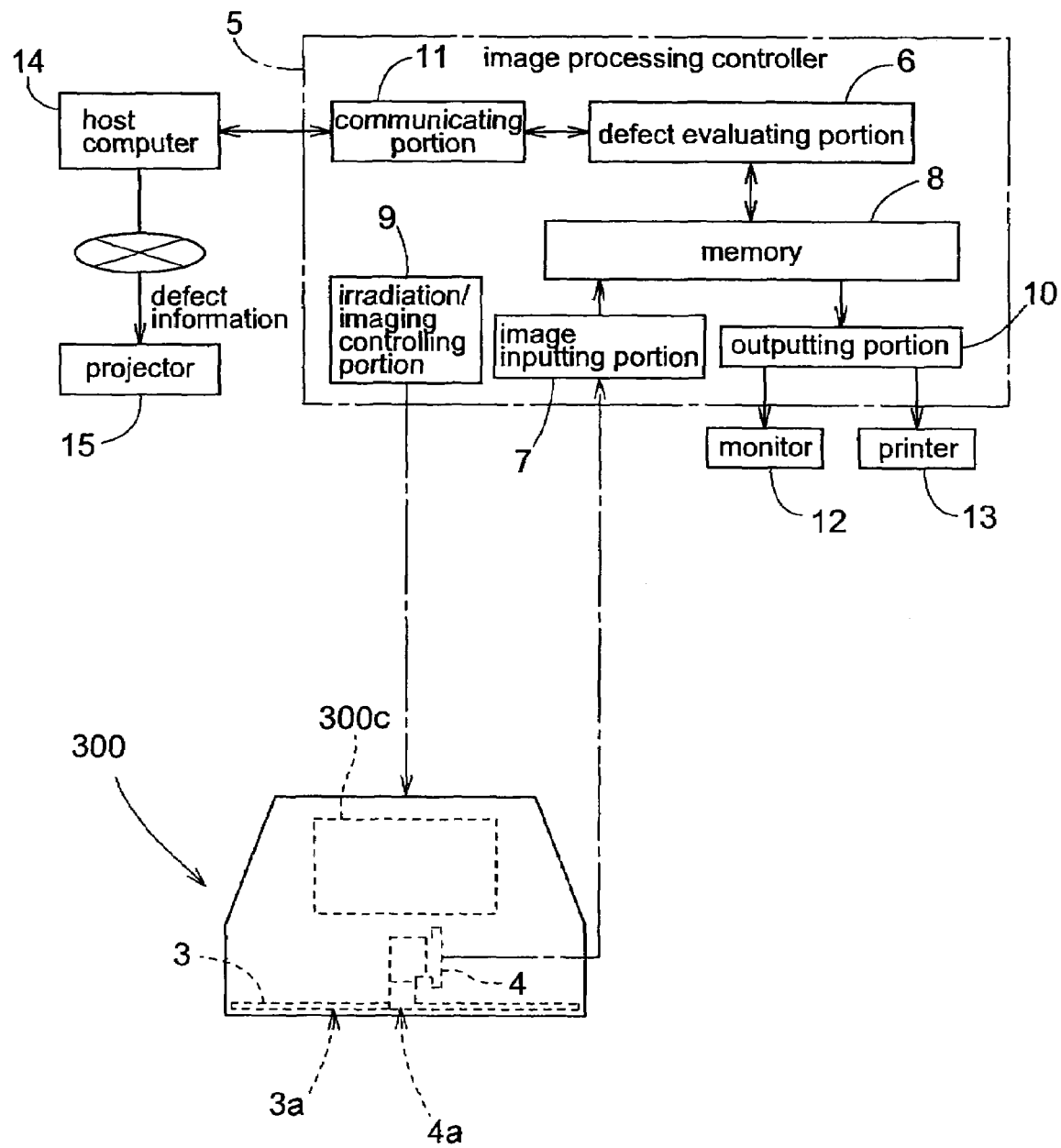
[FIG. 5] a view showing a controlling/information processing unit for the imaging unit of the surface defect inspecting apparatus relating to the present invention.
Figure 6:
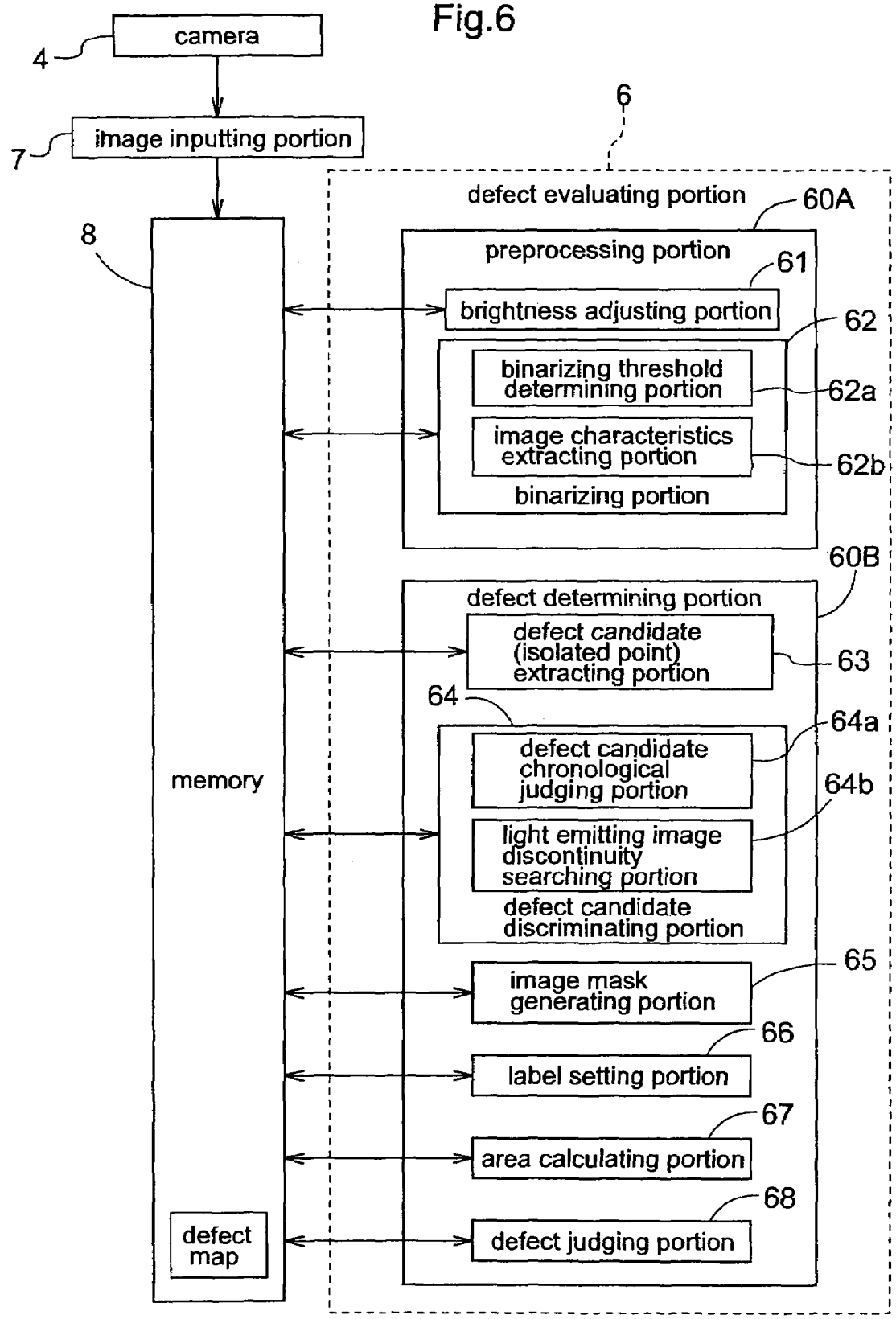
[FIG. 6] a functional block diagram showing the construction of a defect evaluating means incorporated in the surface defect inspecting apparatus.
Figure 7:
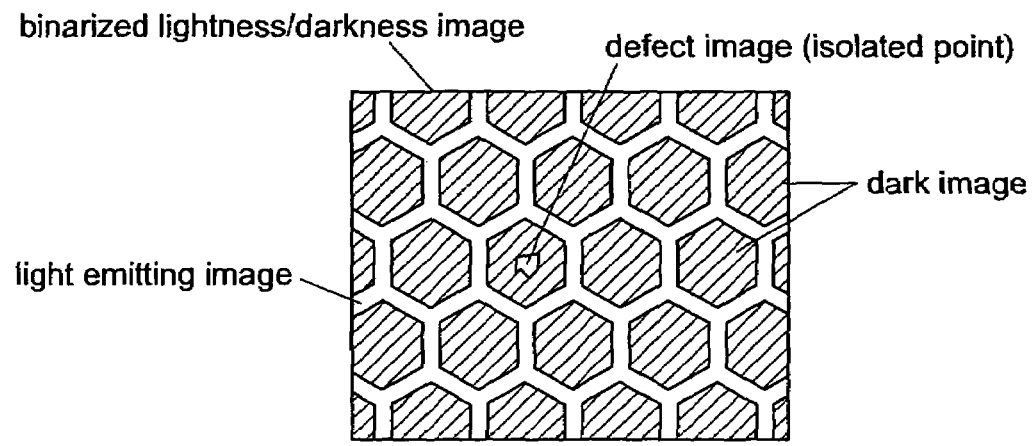
[FIG. 7] an explanatory view explaining a binarized input image.
Figure 8:
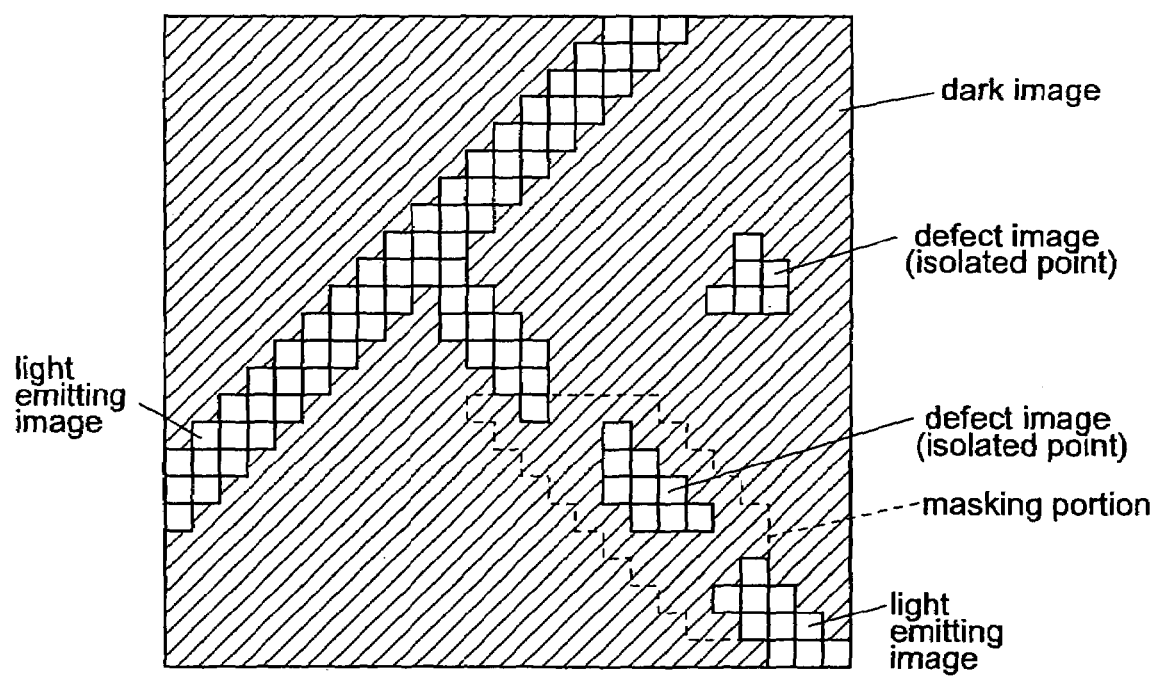
[FIG. 8] an explanatory view explaining an isolated point present at an interrupted portion of light emitting images.
Figure 9:
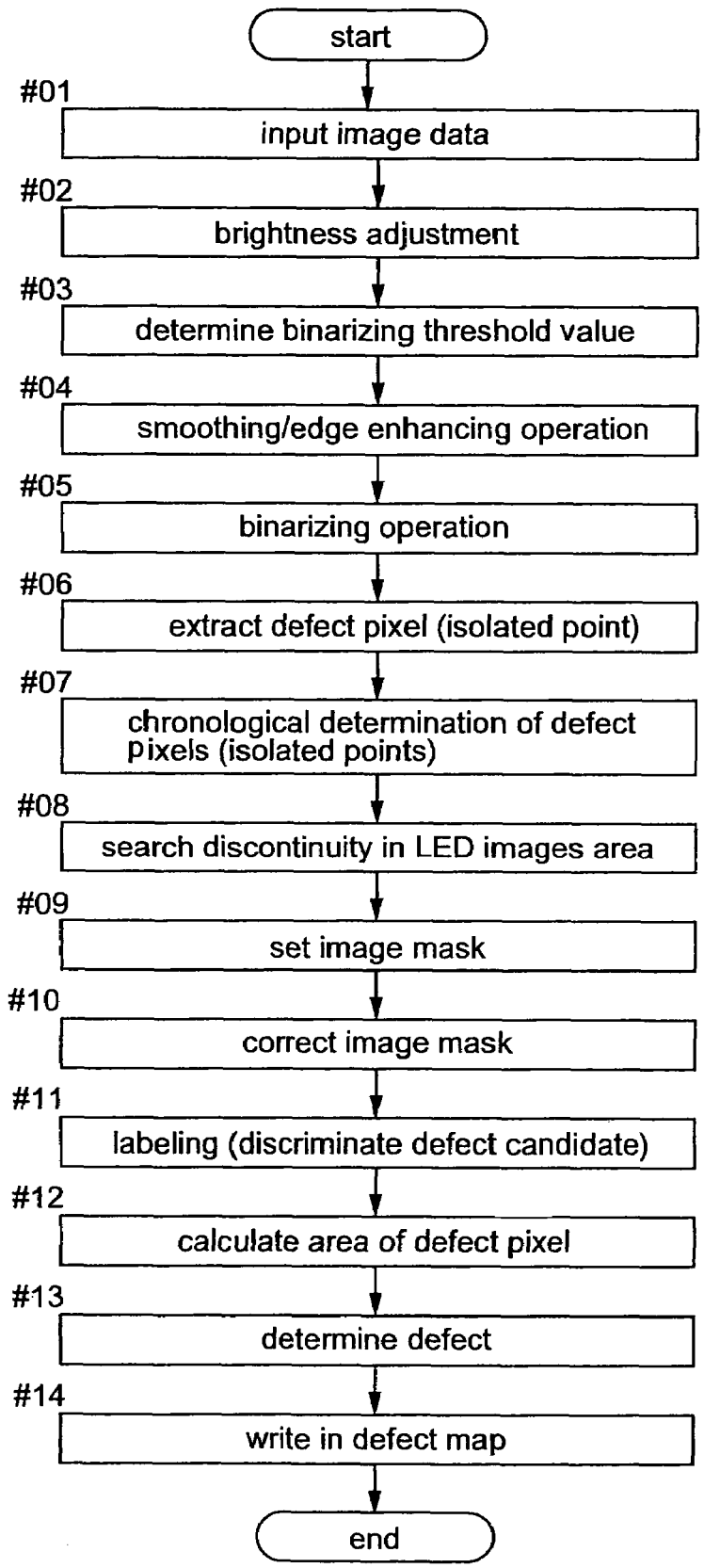
[FIG. 9] a flowchart illustrating process of defect evaluation on an inspection target surface by the defect evaluating means.
Figure 10:
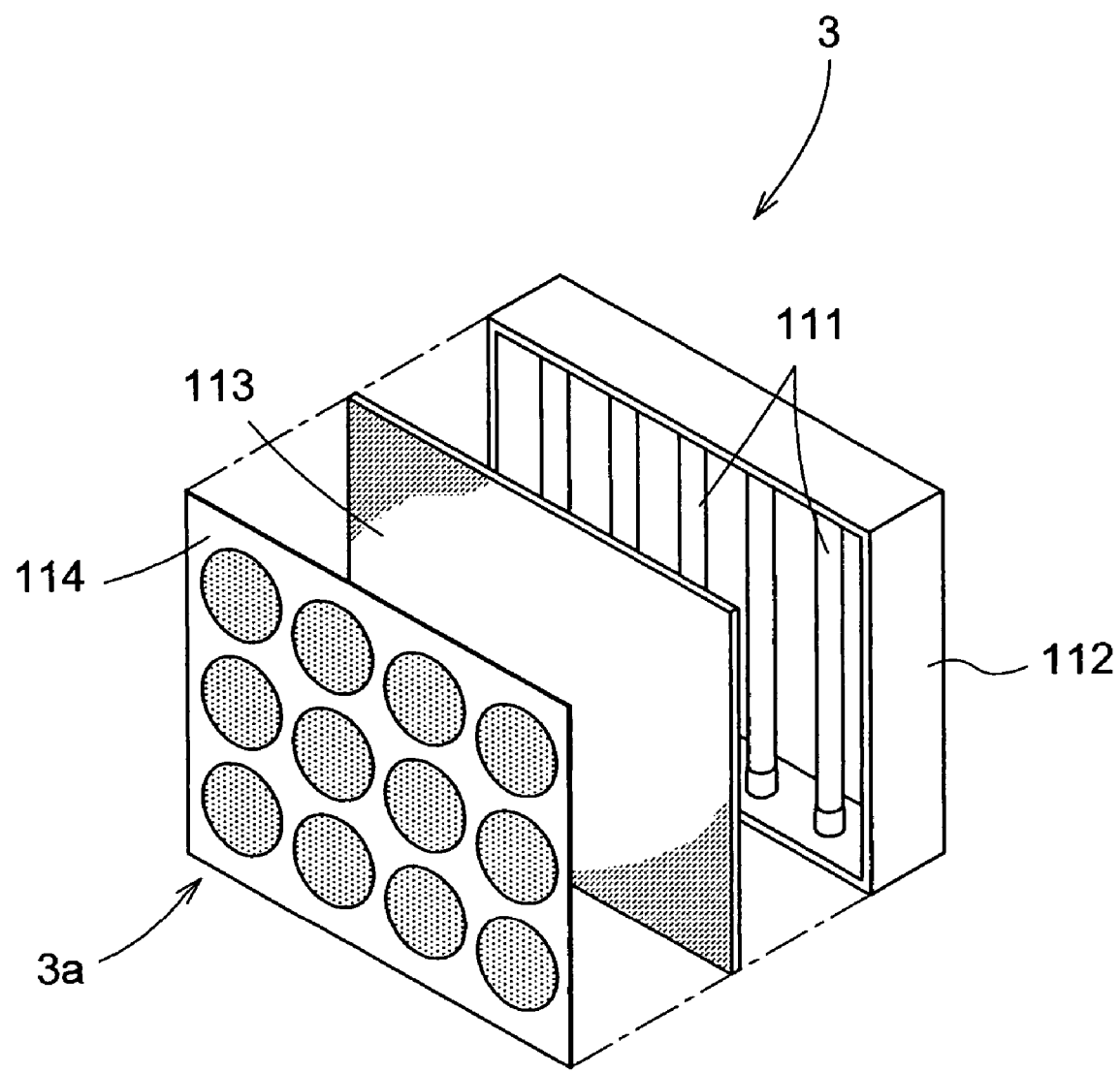
[FIG. 10] a further embodiment in which the irradiation unit comprises fluorescent tubes and a diffuser plate.
Figure 11:
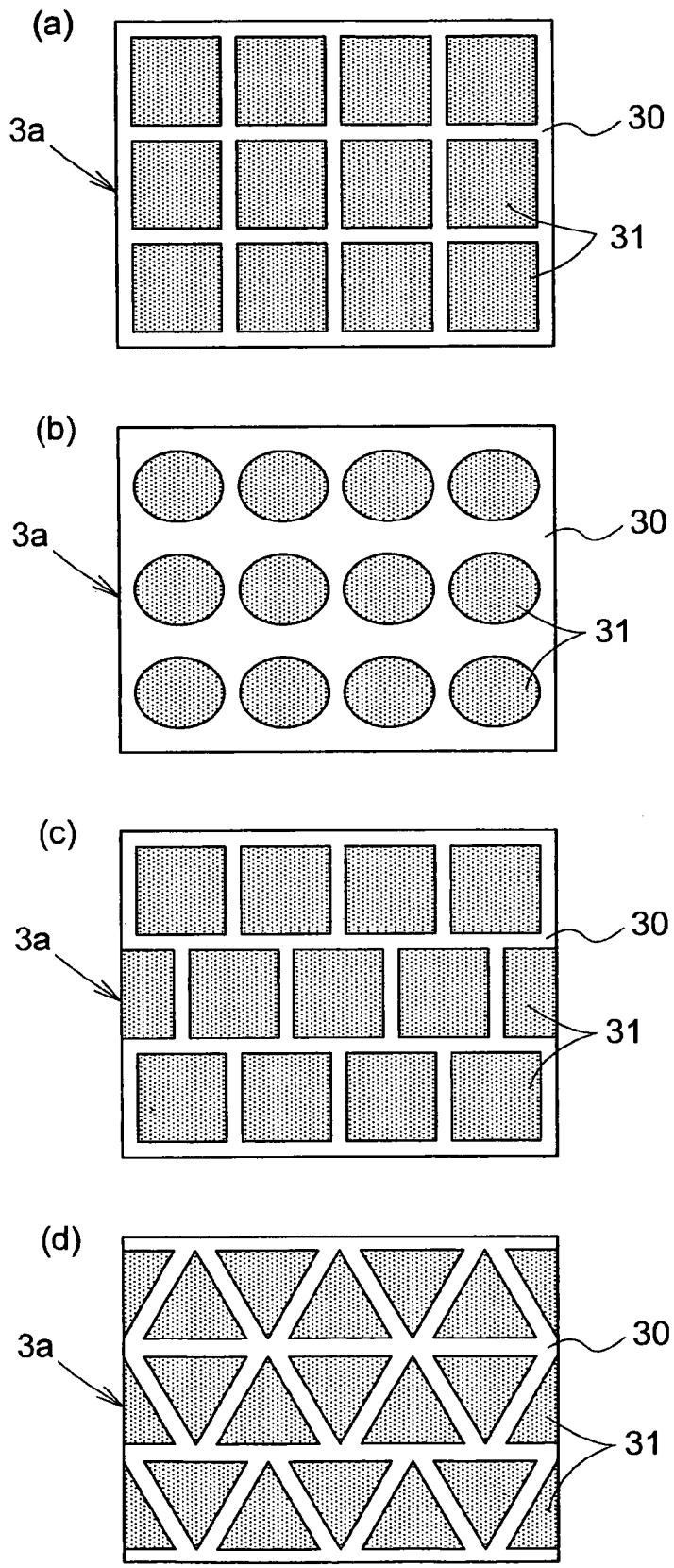
[FIG. 11] an example showing further constructions of dark face.
Figure 12:
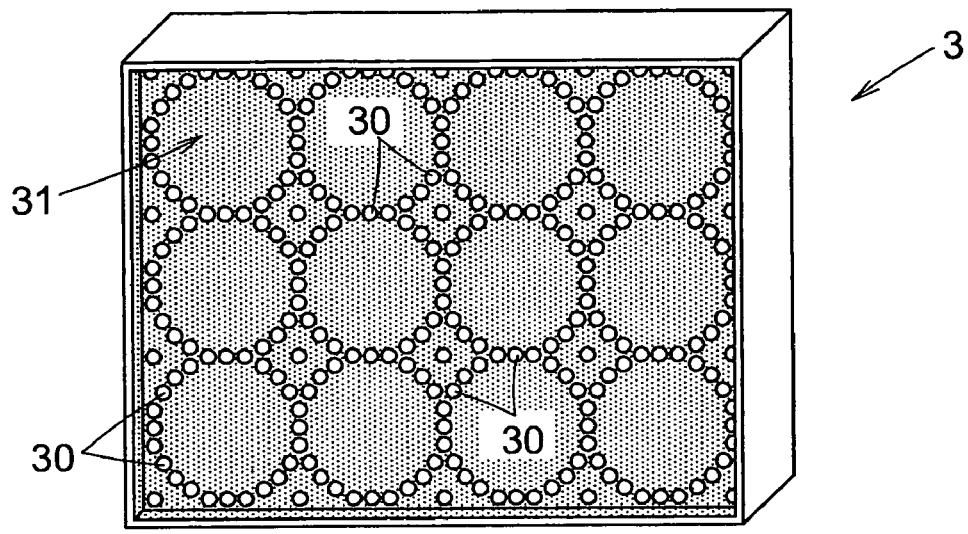
[FIG. 12] an example in which the irradiation unit includes a different arrangement of light emitting elements.
Figure 13:
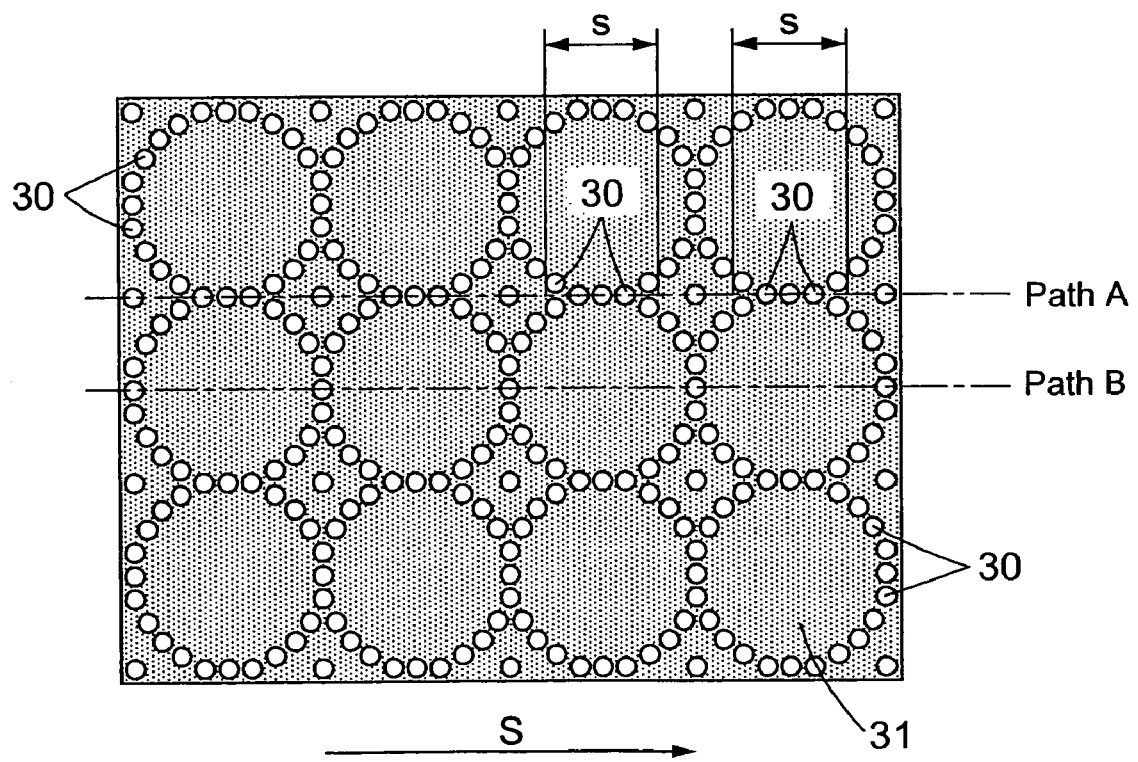
[FIG. 13] a view showing a problem which occurs when the arrangement of light emitting elements shown in FIG. 12 is employed.
Figure 14:
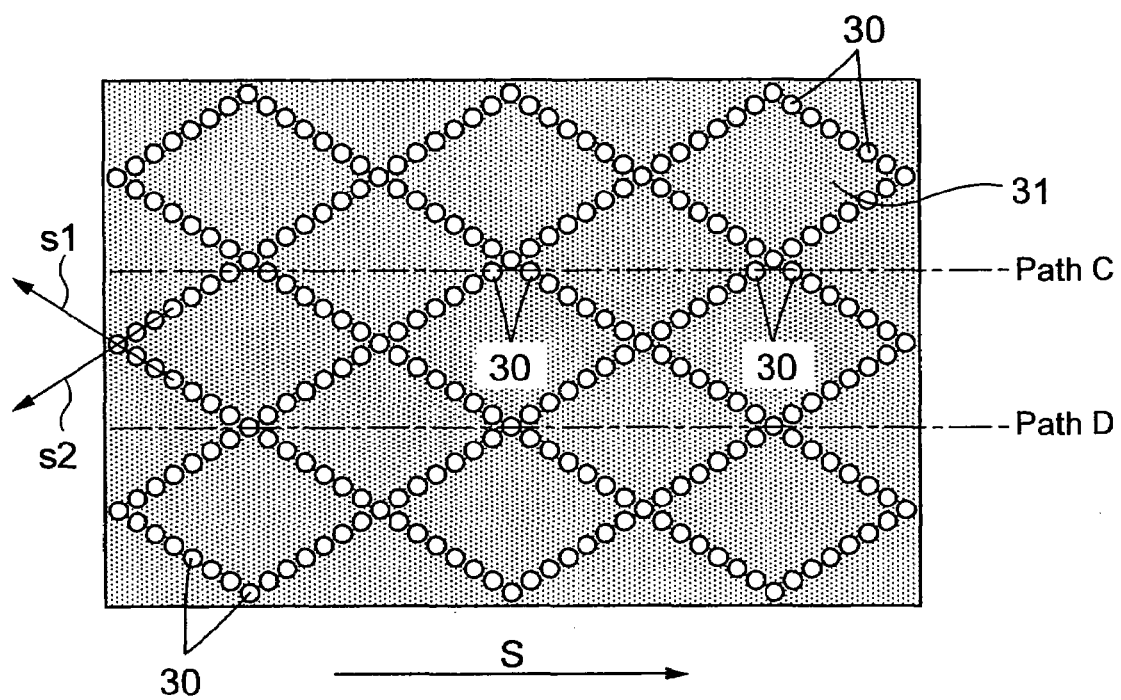
[FIG. 14] a view showing a preferred arrangement of light emitting elements relative to the example shown in FIG. 11.
Figure 17:
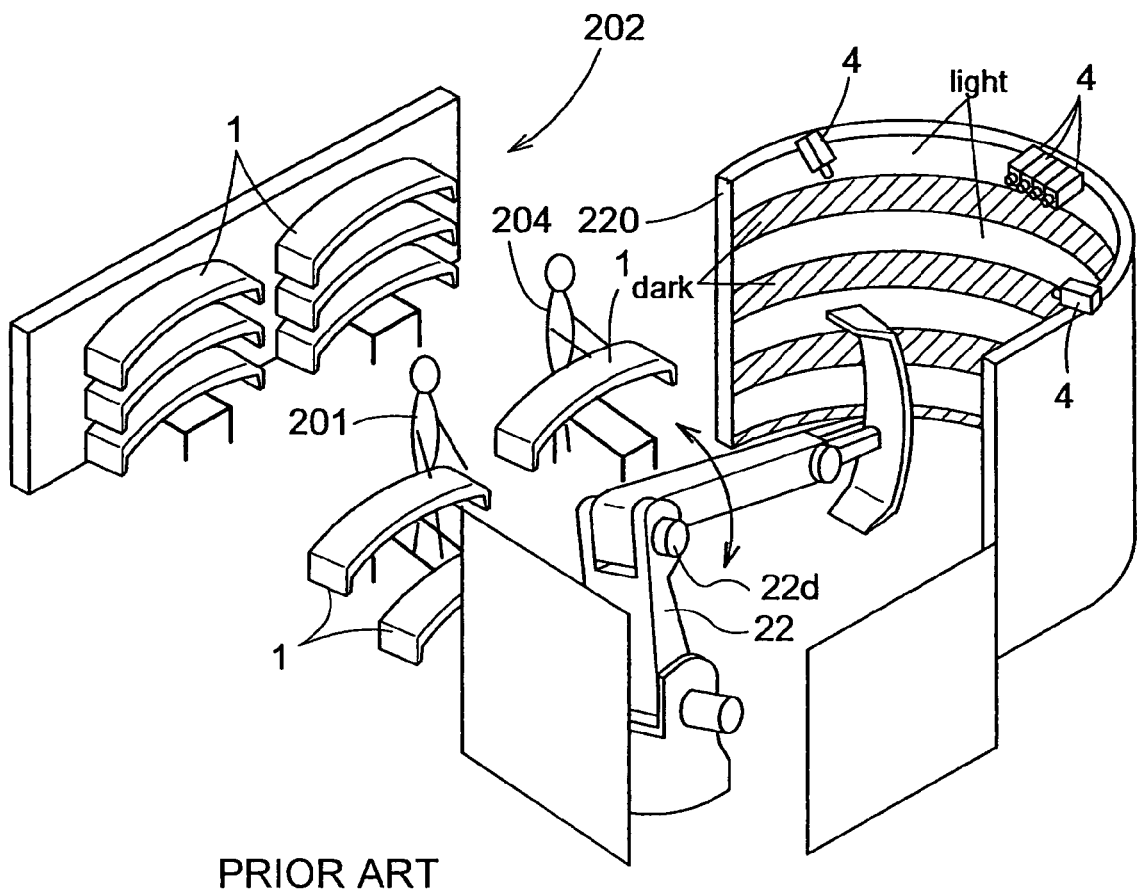
[FIG. 17] a view showing a construction of a bumper inspecting system of the conventional type.
Figure 18:
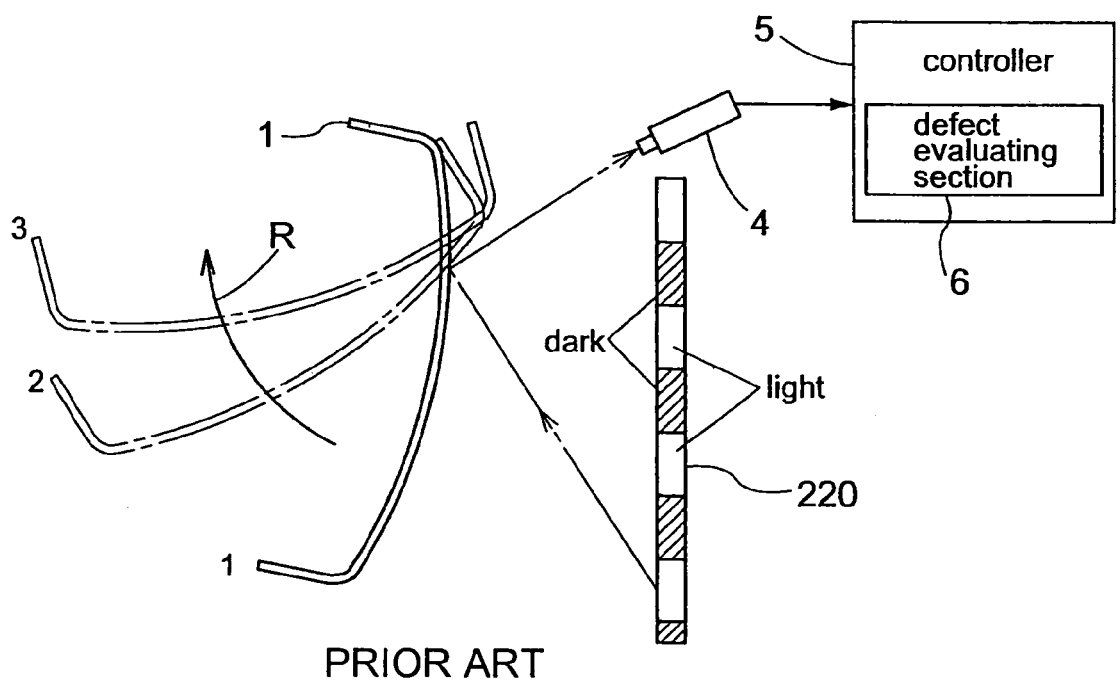
[FIG. 18] an explanatory view of an inspection principle showing a stripe-like irradiation light.

3: irradiation unit
4: imaging camera
5: image processing controller
6: defect evaluating portion (means)

30: light emitting elements (LED elements)
31: dark face
60A: preprocessing portion
60B: defect determining portion
61: brightness adjusting portion
62: binarizing portion
63: defect candidate (isolated point) extracting portion
64: defect candidate discriminating portion
65: image mask generating portion
66: label setting portion
67: area calculating portion
68: defect judging portion

The invention claimed is:

1. A surface defect inspecting method comprising the steps of:
   irradiating an irradiation light having a predetermined pattern on an inspection target surface;
   imaging the surface irradiated with the irradiation light; and
   inspecting the inspection target surface based on an obtained image of the inspection target surface,
      wherein the irradiation light irradiated from an irradiation face has a mesh-like pattern including meshes of a same shape, each mesh having an irradiation area smaller than a non-irradiation area in a plane normal to an optical axis; and
      the inspection target surface is inspected based on lightness/darkness information of an image area in the obtained image corresponding to a non-irradiated area in the inspection target surface.

2. The surface defect inspecting method according to claim 1, wherein if an image obtained is a normal obtained image when the irradiation light is irradiated on a normal inspection target surface and a brightness of the irradiation area in the normal obtained image is defined as a high brightness whereas a brightness of the non-irradiation area is defined as a low brightness; then,
   an intermediate brightness area which is present within the obtained image and which is an area of intermediate brightness between the high brightness and the low brightness is used as a target area.

3. The surface defect inspecting method according to claim 1, wherein an image area corresponding to the irradiation area in the inspection target surface is extracted as continuous light areas, and the continuous light areas are precluded from a target area.

4. The surface defect inspecting method according to claim 1, wherein the image area corresponding to the non-irradiated area of the inspection target surface is extracted for each enclosed dark area, and if an isolated light area is present within the enclosed dark area, the isolated light area is determined as a target area.

5. The surface defect inspecting method according to claim 1, wherein in case the inspection target surface is a curved surface, the mesh-like distribution of the irradiation light from the irradiation face corresponding to a shape of the curved surface of the inspection target surface is set as a circular or a regular polygonal mesh-like pattern in the obtained image.

6. A surface defect inspecting apparatus comprising:
   an irradiating means for irradiating an irradiation light having a predetermined pattern on an inspection target surface;
   an imaging means for imaging the inspection target surface irradiated with the irradiation light; and
   an image processing means for effecting an image processing on an image obtained by the imaging means,
      wherein the irradiating means irradiates, from an irradiation face thereof, an irradiation light having a mesh-like pattern including meshes of a same shape, each mesh having an irradiation area smaller than a non-irradiation area in a plane normal to the optical axis; and
      the image processing means, in the image processing, processes lightness/darkness information of an image area corresponding to a non-irradiated area in the inspection target surface.

7. The surface defect inspecting apparatus according to claim 6, wherein if an image obtained is a normal obtained image when the irradiation light is irradiated on a normal inspection target surface and a brightness of the irradiation area in the normal obtained image is defined as a high brightness whereas a brightness of the non-irradiation area is defined as a low brightness; the image processing means includes an intermediate brightness area extracting means for extracting an intermediate brightness area which is present within the obtained image and which is an area of intermediate brightness between the high brightness and the low brightness.

8. The surface defect inspecting apparatus according to claim 6, wherein the irradiation light of the irradiating means is formed by a plurality of light emitting elements distributed in a mesh-like pattern.

9. The surface defect inspecting apparatus according to claim 6, wherein the irradiation light of the irradiating means is formed through transmission between narrow slits distributed in a mesh-like pattern.

10. The surface defect inspecting apparatus according to claim 6, wherein in correspondence with a curved surface shape of the inspection target surface, the mesh-like distribution of the irradiation light from the irradiation face corresponding to the curved surface shape of the inspection target surface is set as a circular or a regular polygonal mesh-like pattern in the obtained image.

11. A surface inspecting apparatus comprising:
   a plurality of light emitting elements arranged in a predetermined layout pattern;
   an imaging camera for imaging an inspection target surface irradiated with an irradiation light of the light emitting elements; and
   an outputting portion for outputting obtained image information of the imaging camera,
      wherein the layout pattern comprises a mesh-like repetitive layout pattern which repeats a continuous arrangement of the light emitting elements along a predetermined direction thereby leaving a dark face of a predetermined shape therewithin; the imaging camera is disposed so as to receive, on at least one dark face, the irradiation light of each light emitting element reflected off an area opposed to the dark face of the inspection target surface; and an emitting area of each of the light emitting elements is smaller than an area of the dark face.

* * * * *

UNITED STATES PATENT AND TRADEMARK OFFICE
CERTIFICATE OF CORRECTION

PATENT NO. : 7,599,050 B2  Page 1 of 1
APPLICATION NO. : 10/576486
DATED : October 6, 2009
INVENTOR(S) : Ishikawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this

Twenty-eighth Day of September, 2010

David J. Kappos
*Director of the United States Patent and Trademark Office*